(12) United States Patent
McNeely et al.

(10) Patent No.: US 8,727,804 B2
(45) Date of Patent: May 20, 2014

(54) COMBINED POWER AND DATA CORD AND RECEPTACLE

(75) Inventors: Craig A. McNeely, Columbus, IN (US); Richard H. Heimbrock, Cincinnati, OH (US); Carl W. Riley, Milan, IN (US); Keith A. Huster, Sunman, IN (US); Irvin J. Vanderpohl, III, Greensburg, IN (US); Paul J. McDaniel, III, Holly Springs, NC (US); Williams F. Collins, Jr., Columbus, IN (US); Oscar A. Manguiat, Cincinnati, OH (US); Terry L. Tincher, Lebanon, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 501 days.

(21) Appl. No.: 13/105,443

(22) Filed: May 11, 2011

(65) Prior Publication Data

US 2011/0210833 A1 Sep. 1, 2011

Related U.S. Application Data

(63) Continuation of application No. 12/128,390, filed on May 28, 2008, now Pat. No. 8,272,892, and a continuation of application No. 10/568,918, filed as application No. PCT/US2004/026772 on Aug. 19, 2004, now Pat. No. 7,399,205.

(60) Provisional application No. 60/496,743, filed on Aug. 21, 2003, provisional application No. 60/601,501, filed on Aug. 13, 2004.

(51) Int. Cl.
*H01R 29/00* (2006.01)

(52) U.S. Cl.
USPC ............................ 439/505; 439/502; 439/536

(58) Field of Classification Search
USPC .................................. 439/505, 502, 498, 536
See application file for complete search history.

(56) References Cited

U.S. PATENT DOCUMENTS

| | | | |
|---|---|---|---|
| 2,740,873 A | 4/1956 | Cronk | |
| 2,858,421 A | 10/1958 | Touvet | |
| 3,953,933 A | 5/1976 | Goldstein | |
| 3,987,928 A | 10/1976 | Mori | |
| 4,343,411 A | 8/1982 | Chesnut et al. | |
| 4,465,333 A | 8/1984 | Caserta et al. | |
| 4,678,264 A | 7/1987 | Bowen et al. | |

(Continued)

FOREIGN PATENT DOCUMENTS

| | | |
|---|---|---|
| DE | 197 01 603 | 7/1998 |
| DE | 199 12 395 | 9/2000 |

(Continued)

*Primary Examiner* — Gary Paumen
(74) *Attorney, Agent, or Firm* — Barnes & Thornburg LLP

(57) ABSTRACT

A system for use with a hospital bed having circuitry and a standard AC power outlet spaced from the hospital bed is provided. The system includes a cable assembly couplable to the circuitry of the hospital bed. The cable assembly has power conductors and at least one data conductor. The cable assembly also has a plug including a first power coupler coupled to the power conductors and a first data coupler coupled to the at least one data conductor. The system also includes a second data coupler mountable adjacent the standard AC power outlet. The second data coupler is configured to couple to the first data coupler when the first power coupler is coupled to the standard AC power outlet.

20 Claims, 18 Drawing Sheets

(56) References Cited

U.S. PATENT DOCUMENTS

| | | |
|---|---|---|
| 4,721,358 A | 1/1988 | Faber et al. |
| 4,767,168 A | 8/1988 | Grandy |
| 4,767,181 A | 8/1988 | McEowen |
| 4,835,343 A | 5/1989 | Graef et al. |
| 4,844,582 A | 7/1989 | Giannini |
| 4,903,340 A | 2/1990 | Sorensen |
| 4,924,349 A | 5/1990 | Buehler et al. |
| 4,977,619 A | 12/1990 | Crimmins |
| 4,984,297 A | 1/1991 | Manome |
| 5,033,112 A | 7/1991 | Bowling et al. |
| 5,049,876 A | 9/1991 | Kahle et al. |
| 5,060,303 A | 10/1991 | Wilmoth |
| 5,073,681 A | 12/1991 | Hubben et al. |
| 5,089,974 A | 2/1992 | Demeyer et al. |
| 5,099,346 A | 3/1992 | Lee et al. |
| 5,103,108 A | 4/1992 | Crimmins |
| 5,109,452 A | 4/1992 | Selvin et al. |
| 5,140,659 A | 8/1992 | Minds et al. |
| 5,146,528 A | 9/1992 | Gleim et al. |
| 5,180,886 A | 1/1993 | Dierenbach et al. |
| 5,212,760 A | 5/1993 | Goetz |
| 5,214,526 A | 5/1993 | Tonomura |
| 5,242,315 A | 9/1993 | O'Dea |
| 5,247,380 A | 9/1993 | Lee et al. |
| 5,274,490 A | 12/1993 | Tsushima et al. |
| 5,278,536 A | 1/1994 | Furtaw et al. |
| 5,305,132 A | 4/1994 | Fasen et al. |
| 5,305,133 A | 4/1994 | Cooper et al. |
| 5,321,542 A | 6/1994 | Freitas et al. |
| 5,416,627 A | 5/1995 | Wilmoth |
| 5,456,373 A | 10/1995 | Ford |
| 5,477,010 A | 12/1995 | Buckshaw et al. |
| 5,508,836 A | 4/1996 | DeCaro et al. |
| 5,548,654 A | 8/1996 | Fast |
| 5,561,412 A | 10/1996 | Novak et al. |
| 5,579,001 A | 11/1996 | Dempsey et al. |
| 5,594,786 A | 1/1997 | Chaco et al. |
| 5,596,648 A | 1/1997 | Fast |
| 5,617,236 A | 4/1997 | Wang et al. |
| 5,657,201 A | 8/1997 | Kochis |
| 5,675,125 A | 10/1997 | Hollinger |
| 5,696,861 A | 12/1997 | Schimmeyer et al. |
| 5,699,038 A | 12/1997 | Ulrich et al. |
| 5,706,110 A | 1/1998 | Nykanen |
| 5,723,817 A | 3/1998 | Arenas et al. |
| 5,811,729 A | 9/1998 | Rintz |
| 5,811,730 A | 9/1998 | Rintz |
| 5,813,873 A | 9/1998 | McBain et al. |
| 5,838,223 A | 11/1998 | Gallant et al. |
| 5,838,471 A | 11/1998 | Beard |
| 5,874,693 A | 2/1999 | Rintz |
| 5,877,820 A | 3/1999 | Yamamuro et al. |
| 5,895,888 A | 4/1999 | Arenas et al. |
| 5,907,419 A | 5/1999 | Martnelli et al. |
| 5,910,776 A | 6/1999 | Black |
| 5,949,567 A | 9/1999 | Jebens |
| 5,967,840 A | 10/1999 | Rose et al. |
| 5,982,519 A | 11/1999 | Martnelli et al. |
| 5,994,998 A | 11/1999 | Fisher et al. |
| 5,995,253 A | 11/1999 | Flaherty |
| 5,998,735 A | 12/1999 | Patterson, Jr. |
| 6,027,367 A | 2/2000 | Woertz et al. |
| 6,051,787 A | 4/2000 | Rintz |
| 6,071,015 A | 6/2000 | Erbse et al. |
| 6,117,076 A | 9/2000 | Cassidy |
| 6,140,911 A | 10/2000 | Fisher et al. |
| 6,147,592 A | 11/2000 | Ulrich et al. |
| 6,183,101 B1 | 2/2001 | Chien |
| 6,193,655 B1 | 2/2001 | McGrath |
| 6,259,355 B1 | 7/2001 | Chaco et al. |
| 6,281,440 B1 | 8/2001 | Baldwin et al. |
| 6,304,600 B1 | 10/2001 | Chiba |
| 6,329,906 B1 | 12/2001 | Fisher et al. |
| 6,355,885 B1 | 3/2002 | Rintz et al. |
| 6,362,725 B1 | 3/2002 | Ulrich et al. |
| 6,434,187 B1 | 8/2002 | Beard et al. |
| 6,442,145 B1 | 8/2002 | De Lange et al. |
| 6,445,299 B1 | 9/2002 | Rojas, Jr. |
| 6,457,874 B1 | 10/2002 | Clapp, Jr. et al. |
| 6,486,792 B1 | 11/2002 | Moster et al. |
| 6,493,121 B1 | 12/2002 | Althaus |
| 6,496,105 B2 | 12/2002 | Fisher et al. |
| 6,500,026 B2 | 12/2002 | Yamaguchi |
| 6,504,633 B1 | 1/2003 | Hovorka et al. |
| 6,504,635 B1 | 1/2003 | Nakashima |
| 6,514,652 B2 | 2/2003 | Cash, Jr. |
| 6,533,466 B1 | 3/2003 | Smith |
| 6,544,075 B1 | 4/2003 | Liao |
| 6,544,200 B1 | 4/2003 | Smith et al. |
| 6,545,218 B1 | 4/2003 | Blaess |
| 6,552,888 B2 | 4/2003 | Weinberger |
| 6,558,045 B2 | 5/2003 | Yamaguchi |
| 6,563,618 B1 | 5/2003 | Morrow et al. |
| 6,585,431 B1 | 7/2003 | Okamoto |
| 6,599,025 B1 | 7/2003 | Deutsch |
| 6,608,253 B1 | 8/2003 | Rintz |
| 6,609,166 B1 | 8/2003 | Nakashima |
| 6,659,947 B1 | 12/2003 | Carter et al. |
| 6,668,328 B1 | 12/2003 | Bell |
| 6,688,779 B2 | 2/2004 | Nishita |
| 6,763,195 B1 | 7/2004 | Willebrand et al. |
| 7,039,456 B2 | 5/2006 | Chen |
| 7,049,524 B2 | 5/2006 | Belli et al. |
| 7,068,143 B2 | 6/2006 | Doering et al. |
| 7,127,738 B1 | 10/2006 | Jackson |
| 7,150,655 B2 | 12/2006 | Mastrototaro et al. |
| 7,177,673 B2 | 2/2007 | Matsumura et al. |
| 7,244,150 B1 | 7/2007 | Brase et al. |
| 7,399,205 B2 * | 7/2008 | McNeely et al. ............ 439/577 |
| 8,608,505 B2 * | 12/2013 | Mantay et al. ............... 439/505 |
| 2002/0004336 A1 | 1/2002 | Yamaguchi |
| 2002/0012329 A1 | 1/2002 | Atkinson et al. |
| 2002/0014951 A1 | 2/2002 | Kramer et al. |
| 2002/0021209 A1 | 2/2002 | Fisher et al. |
| 2002/0023121 A1 | 2/2002 | Sugiyama et al. |
| 2002/0032812 A1 | 3/2002 | Ito |
| 2002/0039068 A1 | 4/2002 | Holowick |
| 2002/0060624 A1 | 5/2002 | Zhang |
| 2002/0067282 A1 | 6/2002 | Moskowitz et al. |
| 2002/0091843 A1 | 7/2002 | Vaid |
| 2002/0101349 A1 | 8/2002 | Rojas, Jr. |
| 2002/0101861 A1 | 8/2002 | Gancarcik et al. |
| 2002/0142650 A1 | 10/2002 | Clark et al. |
| 2002/0149822 A1 | 10/2002 | Stroud |
| 2002/0179092 A1 | 12/2002 | Swennen et al. |
| 2003/0006881 A1 | 1/2003 | Reyes |
| 2003/0016419 A1 | 1/2003 | Palmer et al. |
| 2003/0025601 A1 | 2/2003 | Gruteser et al. |
| 2003/0039257 A1 | 2/2003 | Manis et al. |
| 2003/0052770 A1 | 3/2003 | Mansfield, Jr. et al. |
| 2003/0052787 A1 | 3/2003 | Zerhusen et al. |
| 2003/0058085 A1 | 3/2003 | Fisher et al. |
| 2003/0062990 A1 | 4/2003 | Schaeffer, Jr. et al. |
| 2003/0062991 A1 | 4/2003 | Fisher et al. |
| 2003/0153387 A1 | 8/2003 | Small et al. |
| 2003/0185515 A1 | 10/2003 | Lubkert et al. |
| 2003/0223756 A1 | 12/2003 | Tatum et al. |
| 2003/0227900 A1 | 12/2003 | Watanabe |
| 2004/0091270 A1 | 5/2004 | Choi et al. |
| 2005/0033124 A1 | 2/2005 | Kelly et al. |
| 2005/0208825 A1 * | 9/2005 | Chan ........................... 439/505 |
| 2007/0141869 A1 * | 6/2007 | McNeely et al. ............ 439/76.1 |
| 2008/0224861 A1 | 9/2008 | McNeely et al. |
| 2012/0028488 A1 * | 2/2012 | Puschnigg et al. ............ 439/189 |

FOREIGN PATENT DOCUMENTS

| | | |
|---|---|---|
| DE | 200 15 392 | 5/2001 |
| WO | WO 00/37978 | 6/2000 |
| WO | WO 2005/022692 | 3/2005 |

* cited by examiner

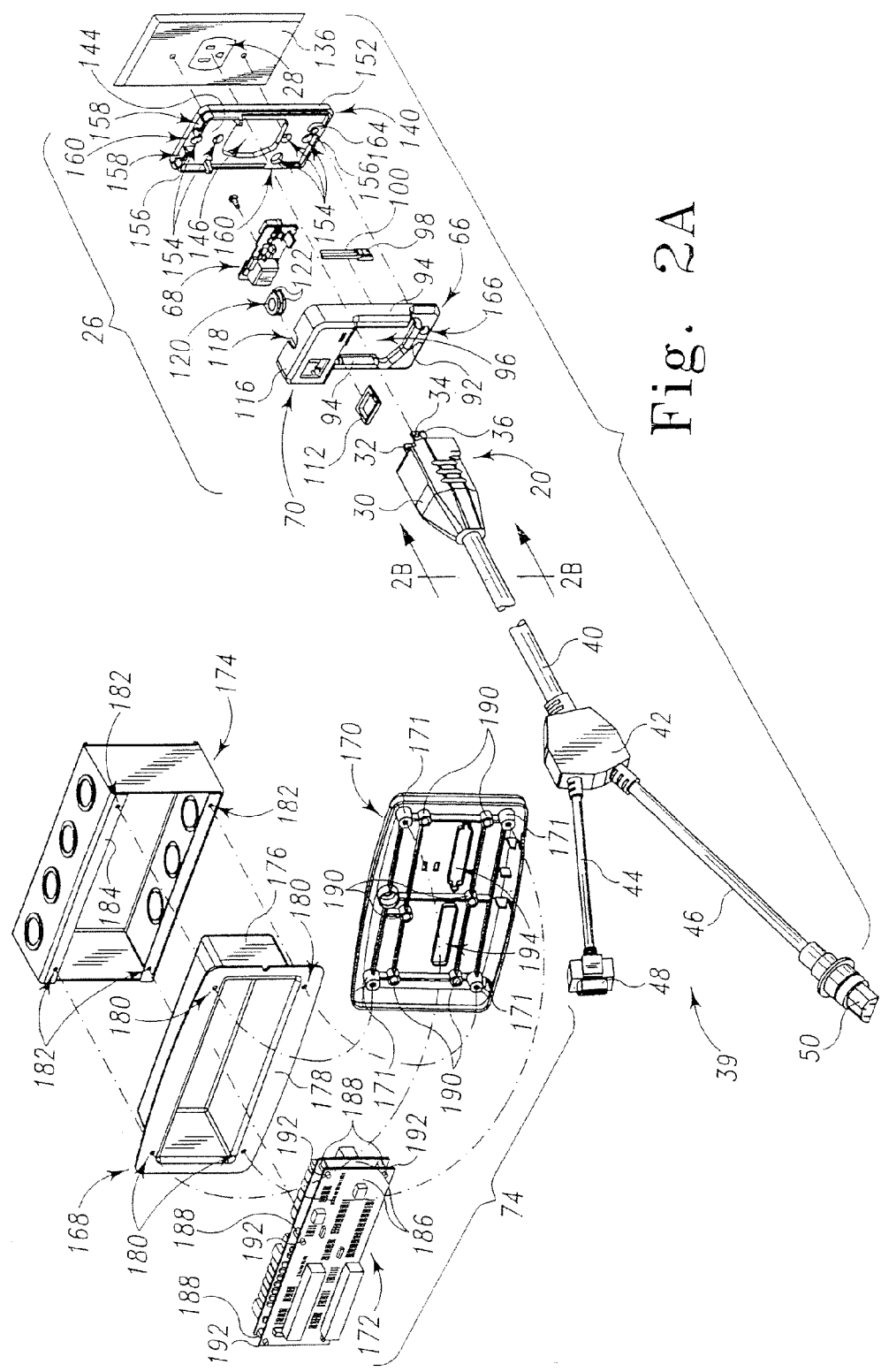

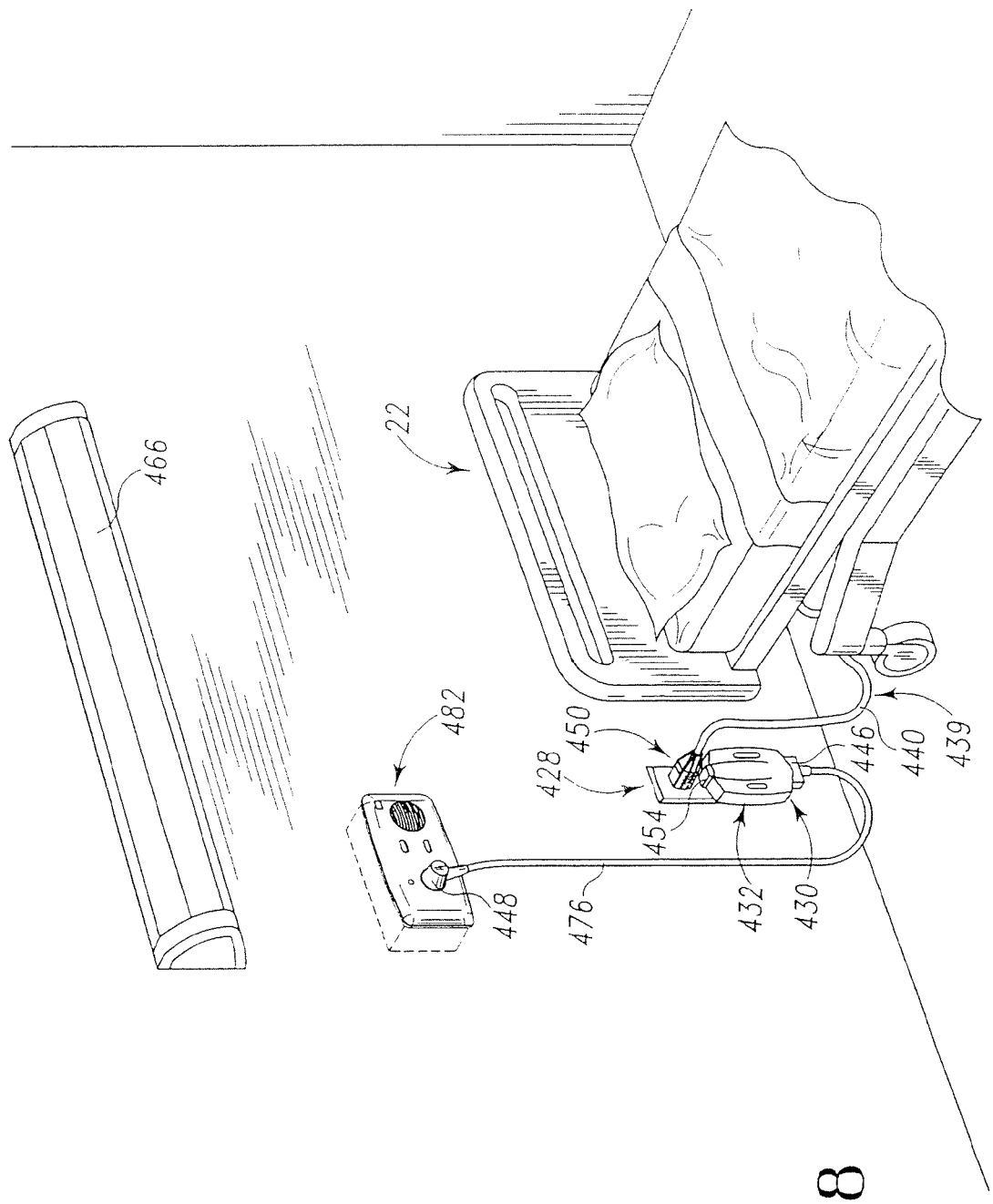

COMBINED POWER AND DATA CORD AND RECEPTACLE

CROSS-REFERENCE TO RELATED APPLICATIONS

This application is a continuation of U.S. application Ser. No. 12/128,390, filed May 28, 2008, which is a continuation of U.S. application Ser. No. 10/568,918, filed Feb. 17, 2006, now U.S. Pat. No. 7,399,205, which is a U.S. national application under 37 C.F.R. §371(b) of International Application Serial No. PCT/US2004/026772 filed Aug. 19, 2004, which claims the benefit, under 35 U.S.C. §119(e), of U.S. Provisional Patent Application Ser. No. 60/496,743 filed Aug. 21, 2003 and U.S. Provisional Patent Application Ser. No. 60/601,501 filed Aug. 13, 2004 each of the foregoing applications being hereby expressly incorporated by reference herein.

BACKGROUND OF THE INVENTION

The present disclosure relates to connectors having wired and wireless couplings. The present disclosure also relates to apparatus for transferring data from a hospital bed to a network of computer devices in a healthcare facility, but has use in other applications and in other environments as well.

Power plugs and/or power receptacles, such as standard 3-prong AC power plugs and receptacles, having electrical and optical couplings are known. See, for example, U.S. Pat. Nos. 6,533,466; 6,071,015; 5,967,840; 5,696,861; and 4,767, 181. Other types of plugs and receptacles having electrical and optical couplings that are also known. See, for example, U.S. Pat. Nos. 5,242,315; 5,109,452; 4,721,358; 4,678,264; 4,465,333; and 4,767,168.

Many devices have a need for both power and data. Typically, such devices have a power cord that couples to a standard power outlet or receptacle and a separate data cable or cord that connects to a data port or receptacle. Having two connections requires that both cables must be disconnected and then reconnected every time the device is moved to a new location. Data connectors or plugs usually have small connector pins that may be damaged during connection or disconnection from an associated receptacle.

In the healthcare environment, many hospital beds receive power from standard wall outlets which may be mounted to a room wall or other architectural equipment, such as a headwall, a bed locator, a column, an arm, and so forth. Thus, a power cord extends between the hospital bed and the wall outlet. Many conventional hospital beds have a separate data port or data cable that connects to a data port mounted to the room wall, headwall, bed locator, etc. Thus, a data cable separate from the power cord extends between the hospital bed and the associated data port or receptacle. Data from the hospital bed is communicated to a network in the healthcare facility so that other computer devices connected to the network have access to the data from the hospital bed. When such a hospital bed having a power cord and a separate data cable is to be transported to a new location, both the power cord and data cable are disconnected from the associated receptacles prior to bed transport and are reconnected to associated receptacles at the new location.

SUMMARY OF THE INVENTION

A plug and/or a communication module and/or a system and/or an apparatus having, or used with, such a plug and/or communication module is provided and has one or more of the following features or combinations thereof, which alone or in any combination may comprise patentable subject matter:

The plug and/or communication module may be provided with both a wired coupler and a wireless coupler. The wired coupler may comprise electrical contacts, such as electrically conductive prongs or sockets or portions thereof. The wireless coupler may comprise one or more of the following: a photoemitter, a photodetector, a photodiode, a radio frequency (RF) transmitter, an RF receiver, an RF transceiver, an infrared (IR) transmitter, an IR receiver, and an IR transceiver. A portion of the wireless coupler may be included in a communication module that attaches to a standard simplex or duplex power outlet. Data may be wirelessly communicated in accordance with any known data transfer protocol, including but not limited to protocols such as IrDA, spread spectrum (including the Bluetooth protocol), RS232, TCP/IP, USB, and $802.11_X$. The wireless data may be communicated by frequency modulation, including frequency modulated infrared (FMIR).

Both power and data may be delivered via a single cable. Such a cable may have a connector, such as a male plug or a female receptacle, at one end or at both ends. Such a cable may include one or more power wires and one or more data wires extending along the length of the cable. The power wires may couple to power prongs or power sockets of the plug. The data wires may couple to signal-processing circuitry which receives the data via the data wires and transmits the data wirelessly after processing the data. The plug may include a plug body which houses at least some of the signal-processing circuitry. The signal-processing circuitry may be integrated into a standard NEMA power cord and plug. The data may comprise any desired information including but not limited to device status, audio, video, and telephony.

The plug and/or communication module may include, or may be coupled to, components for performing parallel-to-serial conversion, serial-to-parallel conversion, encoding, decoding, digital signal processing, compression and/or decompression (CODEC). The wireless signals communicated between the plug and communication module may be bidirectional signals. The wireless signals may include FMIR signals having different carrier frequencies. The wireless signal from the plug to the communication module may be a mixed signal containing a first signal that is frequency modulated at a first carrier frequency and a second signal that is frequency modulated at a second frequency. The wireless signal from the communication module to the plug may be a mixed signal containing a third signal that is frequency modulated at a third carrier frequency and a fourth signal that is frequency modulated at a fourth carrier frequency.

The communication module may plug into a standard power receptacle. The communication module may have both wired and wireless couplers. The communication module may have a receptacle that receives a plug having both wired and wireless couplers. The communication module may have a housing, a data cable extending from the housing, and power prongs extending from the housing. The power prongs may couple to a power outlet or receptacle. The data cable may couple to a data port or receptacle that is spaced from the power outlet. The power outlet and data port to which the communication module couples may be provided in a healthcare facility on a room wall, on a headwall, on a bed locator, on a column, on an arm, or on any other architectural structure. The plug that couples to the communication module may provide connectivity for a hospital bed to power and data. The communication module may include a port configured to couple to a connector of a hospital bed pendant controller and/or to a connector of a data cable extending from a hospital bed.

A method for installing and/or using a plug and/or a communication module is also disclosed and has one or more of the following features or combinations thereof, which alone or in any combination may comprise patentable subject matter:

The method may comprise coupling a combined power-and-data cable to a device. The method may further comprise coupling a plug having a wireless transceiver to a power outlet. The method may comprise placing near the power outlet a communication module having a wireless transceiver that communicates with the wireless transceiver of the plug. The method may comprise coupling the communication module to a data port of the computer network.

Additional features, which alone or in combination with any other feature(s), such as those listed above, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which:

FIG. 2A is an exploded perspective view showing the outlet module having a mounting plate which mounts over an existing outlet cover of a simplex outlet, a housing which carries circuitry and couples to the mounting plate, the plug being insertable into the wall outlet through openings in the mounting plate and housing, the power-and-data cord having a junction body spaced from the plug, a combined data-and-power cord portion extending between the plug and the junction body, separate data and power cord portions extending from the junction body, and the wall module having a circuit board which is received in a housing that is mountable to an electrical junction box;

FIG. 8 is a perspective view showing a hospital bed having an alternative embodiment of a power-and-data cord terminating at a power-and-data plug that is plugged into a first outlet of a wall duplex outlet, an alternative embodiment of an outlet module plugged into a second outlet of the wall duplex outlet for communicating wirelessly with circuitry carried by the plug, and a data cable extending from the outlet module to a patient station of a nurse call system;

DETAILED DESCRIPTION OF THE DRAWINGS

Figure 1:
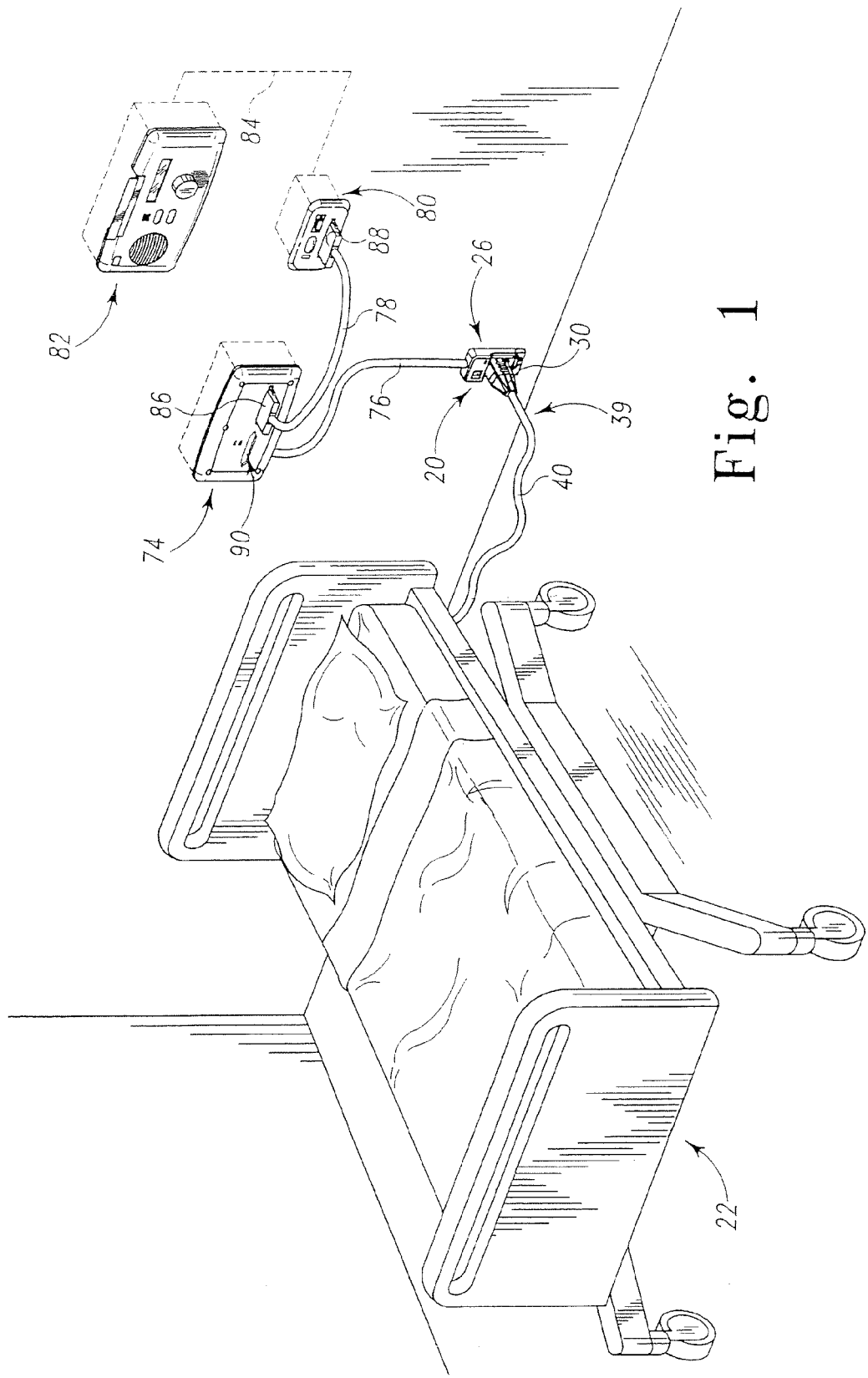
FIG. 1 is a perspective view showing a hospital bed having a power-and-data cord terminating at a power-and-data plug that is plugged into a wall outlet, an outlet module adjacent the outlet for communicating wirelessly with circuitry carried by the plug, a wall module above the outlet module and coupled thereto by a data cord, and a data cable extending from the wall module to an interface unit of a nurse call system which is located beneath a patient station of the nurse call system.
Figure 2B:
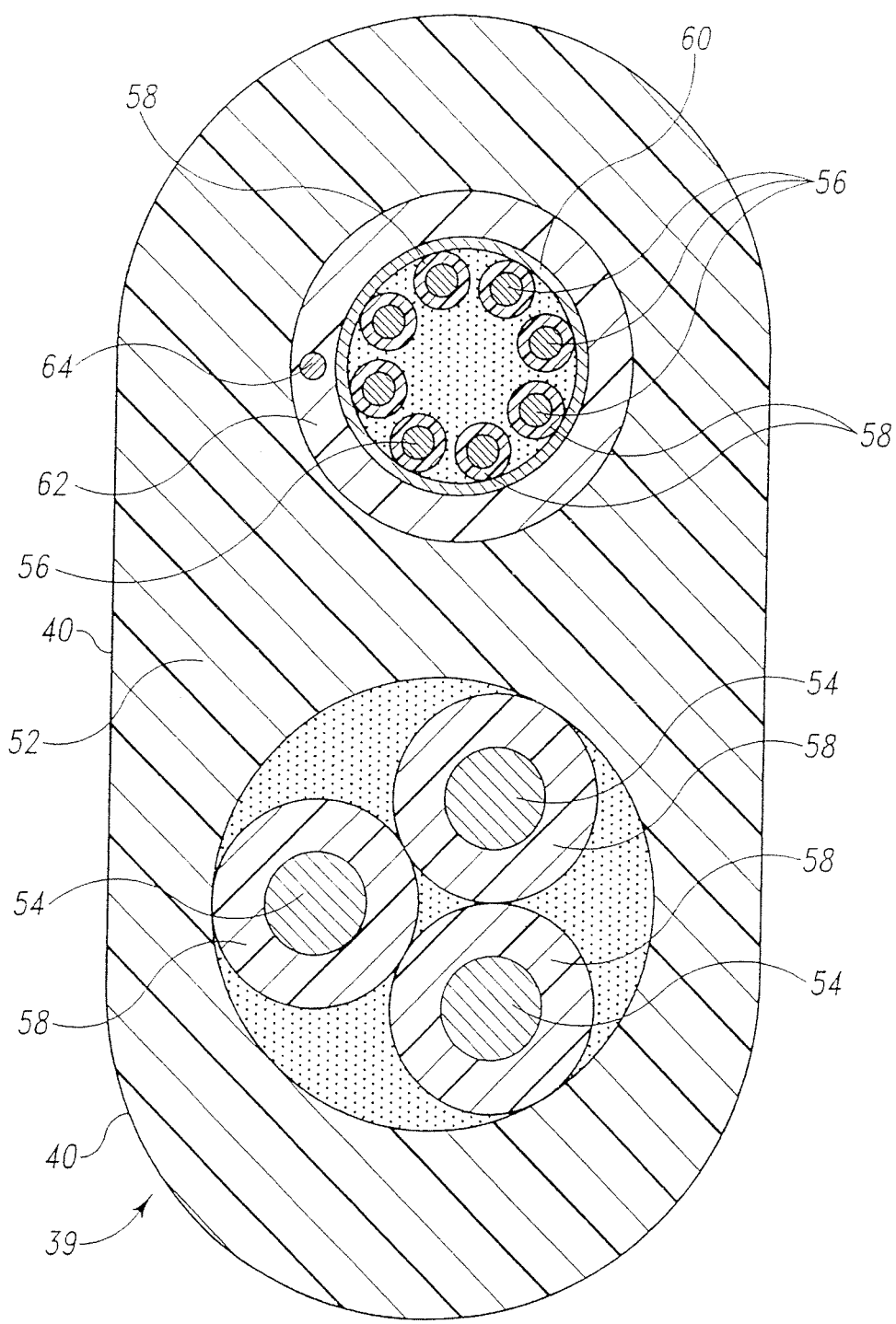
FIG. 2B is a cross-sectional view, taken along line 2B-2B of FIG. 2A, showing the combined data-and-power portion having three power conductors grouped together and a set of data conductors grouped together above the power conductors.
Figure 3:
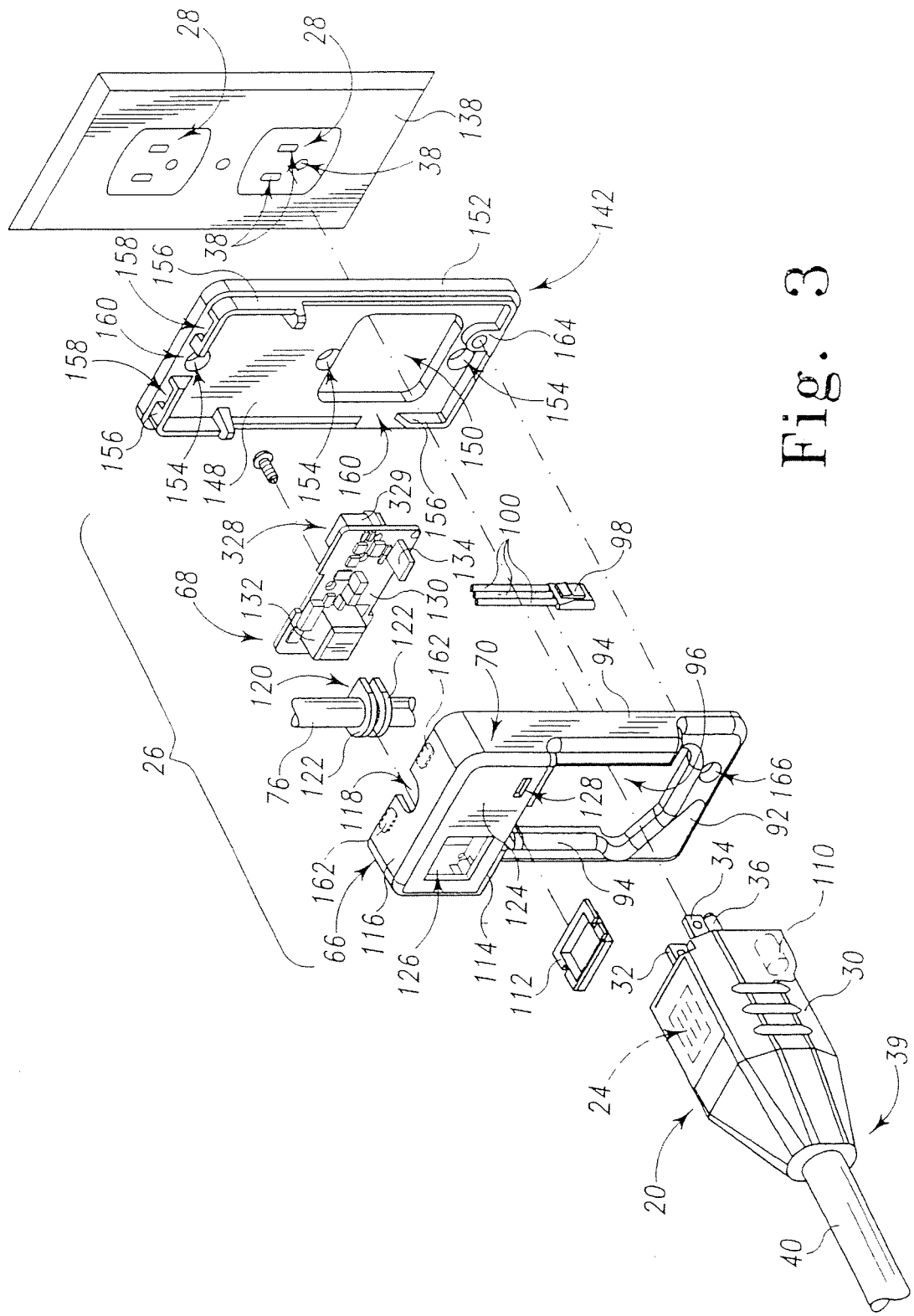
FIG. 3 is an enlarged exploded perspective view of a duplex wall outlet, the outlet module, and the plug.

A power-and-data plug 20 which receives power for a device 22 also includes circuitry 24 for communicating wirelessly with a first communication module 26 that is mounted adjacent a standard AC power outlet or receptacle 28 as shown in FIGS. 1, 2A, and 3. The words "outlet" and "receptacle" are used interchangeably in this disclosure. In the illustrative example, device 22 is a patient-support apparatus, such as a hospital bed. However, the teachings of this disclosure are applicable to all devices which receive power and which transmit and/or receive data. Such devices may include computers of all types, home appliances, industrial equipment, laboratory equipment, data acquisition equipment, monitoring equipment, musical equipment, telecommunications devices, audio equipment, and video equipment, just to name a few. Device 22 is sometimes referred to herein as "bed 22." Communication module 26 is coupled to a computer network with which bed 22 communicates. Because plug 20 is configured to receive power and is configured to communicate wirelessly with module 26, only one connector (i.e., plug 20) is needed to provide both power and data to device 22 and furthermore, only this single connector needs to be unplugged if device 22 is to be moved to a new location.

In the embodiment of FIG. 1, a second communication module 74 communicates with module 26 via a data cord 76. Module 74, in turn, communicates with a computer network via a data cord 78. In the illustrative example, the computer network includes an interface unit 80 and a patient station 82 which are provided in the room adjacent to bed 22. Unit 80 and station 82 are part of a Nurse Call system and communicate via a wired link 84, shown diagrammatically in FIG. 1. Unit 80 and station 82 are coupled to other devices of the computer network of the healthcare facility in a manner well known to those skilled in the art. Additional details of unit 80 and station 82, as well as additional details regarding how these portions of a Nurse Call system connect to other network devices in a healthcare facility are shown and described in U.S. Pat. No. 6,362,725 which is owned by the same assignee as the present application and which is hereby expressly incorporated by reference herein.

In the illustrative embodiment, data cord 78 includes a first 37-pin connector 86 which connects to a 37-pin data port of module 74 and a second 37-pin connector 88 which connects to a 37-pin data port of unit 80 as shown in FIG. 1. The 37-pin data port of unit 80 is an existing data port for connectivity to the computer network of the healthcare facility. Although the data port of unit 80 in the illustrative example receives 37-pin connector 88, it is within the scope of this disclosure to configure module 74 and data cord 78 for connectivity to existing data ports of any configuration having any number of pins or electrical contacts. Module 74 includes a bed data port 90 to which may be coupled a separate data cable (not shown) extending from a bed that does not have a plug, such as plug 20, which is capable of communicating wirelessly with module 26. Such a separate data cable may be coupled to the 37-pin data port of unit 80 instead of port 90, if desired.

The communications links between device 22 and plug 20, between plug 20 and module 26, between module 26 and module 74 and between module 74 and the network are governed by any suitable communications protocol including, but not limited to, protocols such as IrDA, spread spectrum (including the Bluetooth protocol), RS232, TCP/IP, USB, and 802.11$_X$. Furthermore, any one or more of plug 20, device 22, module 26 and module 74 may have circuitry for performing parallel-to-serial conversion, serial-to-parallel conversion, encoding, decoding, digital signal processing, compression and/or decompression (CODEC), or any other type of data processing.

Plug 20 has a plug body 30 in which circuitry 24 is situated as shown in FIG. 3. In the illustrative example, circuitry 24 is situated in a cavity provided in the top of plug body 30. However, it is within the scope of this disclosure for circuitry 24 to be situated anywhere in plug body 30, such as on one of the sides or on the bottom or on the front of plug body 30. Plug 20 has a set of electrical contact members including a first power prong 32, a second power prong 34, and a ground prong 36 as shown in FIG. 3. Prongs 32, 34, 36 extend from the front of plug body 30 in parallel relation and are configured for receipt in associated sockets 38 of outlet 28. Prongs 32, 34, 36 engage electrical contacts (not shown) inside sockets 38 when plug 30 is physically coupled to outlet 28 as is well known in the art. In alternative embodiments, ground prong is omitted from plug 30. In the illustrative example, plug 20 and outlet 28 are made in accordance with National Electrical Manufacturers Association (NEMA) standards relating to devices using 120 V, 60 Hz alternating current (AC) power. However, it is within the scope of this disclosure for plug 20 and outlet 28 to be configured in accordance with any desired standards, such as those used in Europe or standards relating to devices using 220 V AC power, for example.

Plug 20 is included as part of a cable assembly 39 which has a combined power-and-data cable or cord 40 that extends from the back of plug body 30 as shown in FIGS. 1, 2A, and 3. The words "cable" and "cord" are used interchangeably in this disclosure. In the illustrative example, cable 40 extends between the back of plug body 30 and the front of a junction member 42 of cable assembly 39 as shown in FIG. 2A. Cable assembly 39 also has a data cord 44 and a separate power cord 46 that each extend from the back of junction member 42. Data cord 44 terminates at a data connector 48 and power cord 46 terminates at a power connector 50. Data connector 48 is configured to mate with an associated data connector (not shown) of device 22 and power connector 50 is configured to mate with an associated power connector (not shown) of device 22.

Cable 40 comprises a unitary jacket 52, a set of power conductors 54 that are grouped together, and a set of data conductors 56 that are grouped together as shown in FIG. 2B. Power conductors 54 each couple to a respective one of prongs 32, 34, 36. Thus, the power conductor 54 associated with prong 36 is actually coupled to ground when plug 20 is coupled to outlet 28. Data conductors 56 couple to circuitry 24. In the illustrative embodiment, each of conductors 54, 56 comprise metal wires. In alternative embodiments, data conductors 56 are fiber optic lines. In the illustrative embodiment, six of conductors 56 are used as follows: a carrier-in wire, a ground wire associated with the carrier-in wire, a carrier-out wire, a ground wire associated with the carrier-out wire, a power wire, and yet another ground wire. Thus, in the illustrative embodiment, two of the eight conductors 56 are spare wires that are not used. In some embodiments, the six conductors 56 are grouped into three twisted wire pairs with one of the twisted wires of the pair being either the carrier-in wire, the carrier-out wire, or the power and the other of the twisted wires of the pair being a ground wire.

Each of conductors 54, 56 is encased in its own insulator 58. A sheath 60 surrounds data conductors 56 and serves to shield conductors 56, at least partially, from any electromagnetic field(s) produced by the relatively high AC voltage levels associated with power conductors 54. In one embodiment, sheath 60 comprises aluminum and polyethylene, although sheath 60 may comprise any material or materials that are able to shield conductors 56 to some degree. In the illustrative embodiment, a pleach 62 surrounds sheath 60 and a ground conductor 64 is embedded in pleach 62. In alternative embodiments, ground conductor 64 is grouped with conductors 56 within the space surrounded by sheath 60 and, in such embodiments, conductor 64 may have its own insulator similar to insulators 58. In some embodiments, one or both of sheath 60 and pleach 62 are omitted.

As is apparent in FIG. 2B, conductors 54, 56 are embedded in jacket 52 and extend along the length of jacket 52. Conductors 54 and the associated insulators 58 are routed through junction member from jacket 52 to power cord 46. Conductors 56, the associated insulators 58, sheath 60, pleach 62, and ground conductor 64 are routed through junction member 42 from jacket 52 to data cord 44. Thus, junction member 42 serves as a splitter to split the combined power-and-data cord 40 into separate power and data cords 44, 46. In the illustrative embodiment, cords 40, 44, 46 of cable assembly 39 are not intended to be detachable from junction member 42. In alternative embodiments, connectors are provided between one or more of cords 40, 44, 46 and junction member 42 so that the one or more cords 40, 44, 46 to are detachable from junction member 42.

Having separate cords 44, 46 extending from junction member 42, with associated connectors 48, 50 at the ends of cords 44, 46, allows cable assembly 39 to couple to devices having spaced-apart data and power connectors (not shown) which are configured to mate with connectors 48, 50. Thus, devices 22 having completely separate power cords and data cords may be retrofitted with cable assembly 39. In alternative embodiments, a combined power-and-data connector may be provided at the end of cable assembly 39 if the associated device has a mating connector that is appropriately configured to couple with the combined power-and-data connector of assembly 39. In such alternative embodiments, junction member 42 is omitted and cable 40 extends between plug 20 and the combined power-and-data connector. In still other alternative embodiments, device 22 is manufactured such that cable 40 is not intended to be detachable from device 22 but rather extends into a portion of device 22, such as through a strain relief, for example, and then conductors 56 couple to circuitry internal to device 22 by solder connections or a data connector, for example.

As mentioned above, plug 20 has circuitry 24 that communicates wirelessly with communication module 26. Module 26, sometimes referred to herein as the "outlet module," comprises a housing 66 and circuitry 68 that is situated in a cavity provided in an upper portion 70 of housing 66 as shown in FIGS. 2A and 3. In the illustrative embodiment, a bidirectional wireless communications link is established between circuitry 24 and circuitry 68 across a gap 72, shown in FIG. 4, that exists between the top surface of plug body 30 and the bottom surface of part of upper portion 70. In alternative embodiments, a one-way wireless communications link is established between circuitry 24 and circuitry 68. The one-way wireless communications link may be from circuitry 24 to circuitry 68 or vice versa.

In the illustrative example, gap 72 is relatively small, such as one the order of 1 inch (2.54 cm) or less. However, gap 72 may be larger if desired. As long as gap 72 is small enough (i.e., on the order of 1 yard or 1 meter), then short-range transceivers may be used in plug 20 and module 26. If gap 72 is larger, then longer range transceivers are used. This disclosure contemplates that the wireless communications link between circuitry 24 and circuitry 68, be it one-way or bidirectional, may be infrared (IR), radio frequency (RF), ultrasonic, or any other type of wireless communications link. In the illustrative embodiment, data is transmitted wirelessly between circuitry 24 and circuitry 68 via frequency modulated infrared (FMIR) signals as will be described in further detail below.

Housing 66 of module 26 includes a bottom portion 92 and a pair of side portions 94 that interconnect top portion 70 and bottom portion 92 as shown in FIGS. 2A and 3. Thus, a plug-receiving opening 96 is provided in housing 66 and is bounded by portions 70, 92, 94. Top portion 70 protrudes outwardly beyond side portions 94 and is configured to receive a lens 112 adjacent an opening in a bottom wall 114 thereof. Wireless signals communicated between circuitry 24 and circuitry 68 pass through lens 112. In addition, some or all of the top of plug body 30 is made of a material that permits the wireless signals communicated between circuitry 24 and circuitry 68 to pass therethrough. A top wall 116 of portion 70 of housing 66 has a notch 118 which receives data cable 76. A strain relief 120 is coupled to data cable 76 and includes flange portions 122 above and below top wall 116. Forces imparted on the portion of data cable 76 exposed outside of housing 66 are transmitted to top wall 116 of housing by strain relief 120, thereby protecting the integrity of the connection between data wires of cable 76 and circuitry 68.

One of side portions 94 of housing 66 is slightly larger than the other of side portions 94 and has a cavity in which is received a Hall effect sensor 98. Wires 100 are routed from sensor 98 to circuitry 68 situated in upper portion 70 of housing 70. A magnet 110, shown in FIG. 3 (in phantom) is coupled to plug body 30 and is sensed by sensor 98 when plug 20 is plugged into outlet 28. In the illustrative embodiment, magnet 110 is embedded in plug body 30 near one of the sides thereof. In alternative embodiments, magnet 110 is situated elsewhere in plug body 30 and sensor 98 is situated elsewhere in housing 66. In some embodiments, some or all of magnet 110 is situated outside of plug body. If sensor 98 signals circuitry 68 that magnet 110 is sensed, then computer devices coupled to the network, including module 74, are signaled that device 22 is communicating with the network via plug 20 having wireless communication capability.

Figure 4:
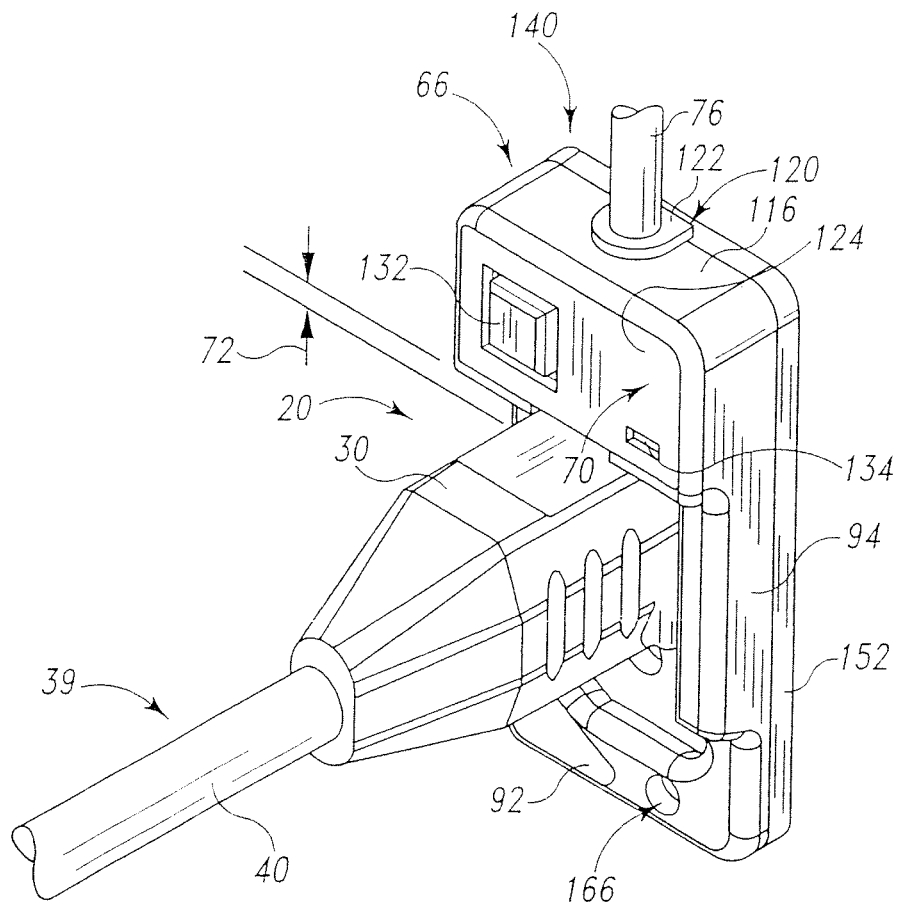
FIG. 4 is an enlarged perspective view, similar to FIG. 3, showing the mounting plate and housing of the outlet module coupled together, the plug inserted through the openings of the outlet module to plug into the wall outlet, and the housing of the outlet module having an upper portion that overhangs a portion of a plug body of the plug to permit wireless communication between circuitry carried by the plug body and circuitry situated in the upper portion of the housing of the outlet module.

A front wall 124 of portion 70 of housing 66 has a large aperture 126 and a small aperture 128 as shown in FIG. 3. Circuitry 68 includes a circuit board 130 that carries a Nurse Call cancel button 132 and a light emitting diode (LED) 134. Button 132 is received by, or is at least accessible through, aperture 126 and LED 134 is received by, or is at least viewable through, aperture 128 as shown in FIG. 4. If sensor 98 senses the presence of magnet 110, thereby indicating that plug 20 is plugged into outlet 28, and then subsequently senses an absence of magnet 110, circuitry 68 will place a Nurse Call signal to the network via module 74 to indicate that plug 20 has been unplugged. Such a Nurse Call signal serves as an alarm that plug 20 may have become unplugged from outlet 28 inadvertently. If a caregiver has intentionally unplugged plug 20 from outlet 28, then the caregiver can press button 132 to cancel the Nurse Call signal generated due to plug 20 being unplugged.

When sensor 98 senses the presence of magnet 110 and when circuitry 68 of module 26 is able to communicate wirelessly with circuitry 24 of plug 20, LED 134 shines green to indicate that plug 20 is plugged into outlet 28 and to indicate successful wireless communication between plug 20 and module 26. If sensor 98 does not sense the presence of magnet 110 or if circuitry 68 is not able to communicate wirelessly with circuitry 24 despite sensor 98 sensing the presence of magnet 110, then LED 134 shines red to indicate an error condition in the communications link between plug 20 and module 26. In alternative embodiments, module 26 may have multiple LED's in lieu of the single LED 134 which is able to shine red or green.

Depending upon whether outlet 28 is a simplex outlet (i.e., one outlet 28) having a simplex cover plate 136, shown in FIG. 2A, or a duplex outlet (i.e., two outlets 28) having a duplex cover plate 138, shown in FIG. 3, illustrative module 26 has either a simplex mounting plate 140 or a duplex mounting plate 142, respectively. Plates 140, 142 mount over plates 136, 138, respectively. Plate 140 has a main portion 144 with a plug-receiving opening 146 that is generally centered between the top and bottom of portion 144 so as to align with outlet 28 in the simplex configuration as shown in FIG. 2A. Plate 142 has a main portion 148 with a plug-receiving opening 150 that is closer to the bottom of portion 148 than the top of potion 148 so as to align with a bottom one of the outlets 28 in the duplex configuration as shown in FIG. 3. Plates 140, 142 each have a peripheral rim 152 extending rearwardly from portions 144, 148, respectively. Rim 152 cooperates with the respective one of portions 144, 148 to define a cavity that is sized to accommodate cover plates 136, 138, respectively, which project slightly away from the wall with which outlets 28 are associated. Thus, illustrative rim 152 surrounds the respective cover plate 136, 138 and engages the associated wall.

Main portions 144, 148 of respective plates 140, 142 each have multiple generally round apertures 154 which are positioned to align with threaded apertures associated with various configurations of outlets 28 and which are configured to receive fasteners, such as screws, therein to mount plates 140, 142 over plates 136, 138, respectively. Thus, fasteners are received in different ones of apertures 154 depending upon the configuration of a particular outlet with which plates 140, 142 are used. A ridge 156 extends forwardly from each of portions 144, 148 and is inset by a slight amount from the outer periphery of portions 144, 148. A pair of generally rectangular apertures 158 are provided in top portions of ridge 156. In the illustrative example, a pair of gaps 160 are provided between portions of ridges 156 of plates 140, 142. The gap 160 between the top portions of ridges 156 is provided to accommodate one of apertures 154 and to permit data cable 76 to pass therethrough. The other of gaps 160 is provided between portions of ridges 156 near one of the sides of respective plates 140, 142 to receive a tool, such as a screwdriver, if needed, to facilitate disassembly of module 26 and, in the case of plate 140 to accommodate one of apertures 154.

Housing 66 is configured to couple to each of plates 140, 142. Thus, although plates 140, 142 are configured differently depending upon whether outlet 28 has a simplex or duplex configuration, the same configuration of housing 66 may be used regardless of whether outlets 28 have a simplex or duplex configuration. In the illustrative embodiment, a pair of fingers or tabs 162 extend downwardly from top wall 116 of housing 66 as shown in FIG. 3 (in phantom). Tabs 162 are received in apertures 158 of ridges 156 of plates 140, 142 when housing 66 is mounted to either of plates 140, 142. Each of plates 142 has a threaded boss 164 and bottom portion 92 of housing 66 has a round aperture 166. A fastener, such as a screw, extends through aperture 166 and threads into boss 164 to retain housing 66 on the associated one of plates 140, 142.

While mounting plates 140, 142 have been discussed above as mounting to outlets 28 and associated plates 136, 138 with fasteners, such as screws, and while housing 66 has been described above as mounting to plates 140, 142 with tabs 162 and fasteners, such as screws, it is within the scope of this disclosure for alternative coupling mechanisms to couple portions of module 26 together or to mount module 26 adjacent to outlet 28. For example, clips, rivets, snaps, fingers, tabs, adhesive, tape, bands, straps, magnets, and the like, as well as combinations of these, are contemplated by this disclosure for coupling portions of module 26 together and for mounting module 26 adjacent to outlet 28. While the illustrative embodiment has module 26 mounted over plates 136, 138 associated with outlets 28, in alternative embodiments, module 26 is mounted to the wall (or any other structure to which outlet 28 is mounted or any other suitable structure in the vicinity of outlet 28) either above, below, or beside cover plates 136, 138 associated with outlets 28. In still other embodiments, cover plates 136, 138 are omitted and module 26, itself, serves as a cover plate for the associated outlet 28.

Opening 96 of housing 66 is large enough to permit opening 146 of plate 140 and opening 150 of plate 142 to align generally with different portions of opening 96. When plug 20 is coupled to outlet 28, a portion of plug 20 is received in opening 96 and in whichever one of openings 146, 150 is in registry with opening 96. Furthermore, the outer peripheries of housing 66 and each of plates 140, 142 have generally the same dimensions so that when housing 66 is coupled to either of plates 140, 142, the top surface of upper portion 70 of housing is generally coplanar with the upper surface of rim 152, the outer side surfaces of side portions 94 are generally coplanar with the side surfaces of rim 152, and the bottom surface of bottom portion 92 is generally coplanar with the bottom surface of rim 152.

In the illustrative embodiment of FIGS. 1-4, the peripheries of housing 66 and plates 140, 142 are generally rectangular, but with rounded corners, and are just slightly larger than the outer periphery of cover plates 136, 140. In addition, module 26 protrudes from the wall associated with outlet 28 by an amount that is roughly about half the length of plug body 30, but having portion 70 overhanging a portion of plug body 30 of plug 20 to permit wireless communication between circuitry 24 carried by plug body 30 and circuitry 68 situated in the upper portion 70 of housing 66. Thus, in the illustrative embodiment of FIGS. 1-4, module 26 is fairly compact in size. Due to the compact size of module 26, some data processing circuitry is situated in module 74 as described in further detail below. It is within the scope of this disclosure, however, for module 26 to have any desired shape.

As mentioned above, communication module 74, which is sometimes referred to herein as the "wall module," communicates with module 26 via data cord 76. Module 74 includes a housing 168, a face plate 170 that couples to housing 168, and circuitry 172 that couples to face plate 170 as shown in FIG. 2A. Housing 168 is configured to mount to a standard electrical junction box 174. Illustratively, housing 168 includes a box portion 176 that is received inside junction box 174 and a flange 178 that extends outwardly from an open front of box portion 176.

Flange 178 has four apertures 180 that generally align with threaded apertures 182 provided in front rails 184 of junction box 174. Face plate 170 has four fastener-receiving bosses 171 that generally align with apertures 180 and apertures 182. Fasteners, such as screws, extend through bosses 171 and through apertures 180 and are threaded into apertures 182 to couple housing 168 and face plate 170 to junction box 174. In lieu of fasteners received by bosses 171 and apertures 180, 182, all types of coupling mechanisms, including, for example, clips, rivets, snaps, fingers, tabs, adhesive, tape, bands, straps, magnets, and the like, as well as combinations of these, are contemplated by this disclosure for coupling housing 168 and face plate 170 to box 174.

Circuitry 172 of module 74 comprises a pair of circuit boards 186 in a back-to-back arrangement and separated by spacers 188 as shown in FIG. 2A. A set of threaded bosses 190 extend from face plate 170, each boss 190 being generally aligned with a corresponding spacer 188. A set of fasteners, illustratively screws 192, extend through spacers 188 and through associated apertures provided in circuit boards 186 and thread into bosses 190 to couple circuitry 172 to face plate 170. Face plate 170 includes a pair of elongated openings 194, one of which aligns generally with bed data port 90 and the other of which aligns generally with the data port to which 37-pin connector couples.

Figure 5:
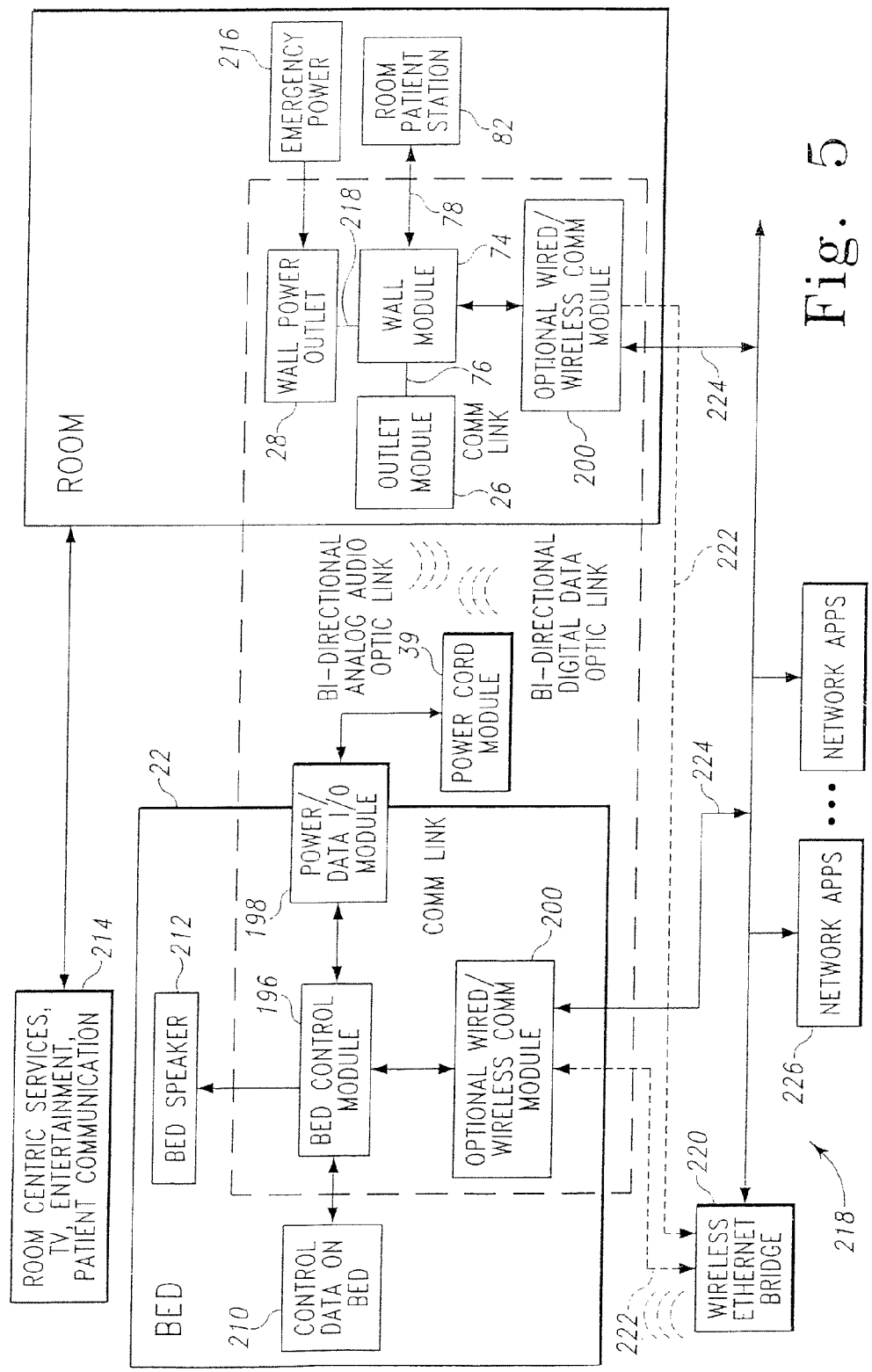
FIG. 5 is a high-level block diagram of various electrical components included in the bed, included in a room, and other devices that communicate with the electrical components included in the bed and the room.

As shown diagrammatically in FIG. 5, bed 22 has a bed control module 196 coupled to a power/data input/output (I/O) module 198. Module 196 comprises circuitry that controls the operation of various functions of bed 22. In addition, module 196 sends and receives control data as indicated at block 210 and is coupled to a bed speaker 212. Examples of the bed functions controlled by module 196 include raising and lowering an upper frame of the bed relative to a base frame of the bed, tilting the upper frame of the bed relative to the base frame, raising and lowering a head section of a mattress-support deck of the bed, raising and lowering a foot section and/or a thigh section of the mattress-support deck of the bed, operating a weigh system of the bed, operating a patient position monitoring (PPM) system of the bed, inflating and deflating air bladders included in the mattress of the bed, and adjusting the volume of speaker 212. Those skilled in the art will appreciate that bed 22 may have other functions which are controlled by module 196 and all of such functions may be controlled by circuitry included in module 196 in accordance with this disclosure.

Examples of control data associated with block 210 include caster braking data (i.e., set or not set), siderail position data (i.e., up or down), bed function lock out data (i.e., whether a caregiver has locked out certain functions of the bed), room light data (i.e., whether one or more lights in a room should be turned on or off), television (TV) control data (i.e., whether a TV should be on or off, whether a TV channel should be changed up or down, whether TV volume should be changed up or down), radio control data (i.e., whether a radio should be on or off, whether a radio channel should be changed up or down, whether radio volume should be changed up or down), Nurse call data (i.e., whether a Nurse call signal has been generated, whether a Nurse call cancel signal has been generated), and microphone control data (i.e., whether a microphone of the bed is on or off). Those skilled in the art will appreciate that bed 22 may have other control data associated therewith and that all of such control data may be communicated to or from module 196 in accordance with this disclosure.

Module 198 is coupled to a power cord module which, in one embodiment, corresponds to cable assembly 39 described above. Therefore, the same reference number (i.e., 39) is used to denote power cord module in FIG. 5 as is used to denote cable assembly 39 in FIGS. 1-4. Module 39 communicates with module 26 via a bidirectional digital data optic link as indicated in FIG. 5. Module 198 comprises circuitry that conditions and converts AC power received from module 39 into direct current (DC) voltage levels, such as ±5 V, ±12 V, ±24 V, etc. for use by circuit components, such as integrated circuit chips, drive motors, relays, and the like, which are included in bed 22. Thus, module 198 comprises circuit components such as transformers, rectifiers, voltage dividers, and voltage regulators, which are typically associated with power circuitry. In addition, one or more of modules 39, 196, 198 also includes signal-processing circuitry. Such signal-processing circuitry may include, for example, circuitry for performing parallel-to-serial conversion, serial-to-parallel conversion, encoding, decoding, digital signal processing, compression and/or decompression (CODEC), or any other type of signal processing. However, the term "signal-processing circuitry" as used in this disclosure, including the claims, is intended to mean broadly circuitry of any and all types that modify, transform, or change a signal.

As also indicated diagrammatically in FIG. 5, the room in which bed 22 is situated has associated therewith room centric services such as TV, entertainment, and patient communication as indicated at block 214. These room centric services, as well as additional services known to those skilled in the art, such as room temperature control and room lighting control, are controlled by signals that originate as control data 210 from user input devices of bed 22. The signals having control data 210 are processed by one or more of modules 39, 196, 198 prior to being communicated wirelessly from module 39 to module 26. The signals having control data 210 are communicated from module 26 to module 74, are processed by one or more of modules 26, 74, and then are communicated either directly from module 74 to the service to be controlled or to the network of the healthcare facility for subsequent communication to the service to be controlled.

Emergency power 216 is coupled to outlet 28 as shown diagrammatically in FIG. 5 and power from outlet 28 is provided to wall module 74 via an electrical coupling 218. It should be understood that the electrical coupling 218 shown diagrammatically in FIG. 5 is intended to indicate that outlet 28 and module 74 receive power from a common power source that delivers power to the room and is not intended to indicate necessarily that module 74 plugs into any of the sockets 38 of outlet 28, although such an embodiment is within scope of this disclosure. In some embodiments, cable 76 includes conductors that deliver power to module 26 from module 74.

According to the embodiment illustrated in FIG. 5, data cable 78 extends from module 78 and couples directly to patient station 82. Thus, in the embodiment of FIG. 5, interface unit 80 is omitted from the communications link between module 74 and station 82. An optional wired and/or wireless communication module 200 may be included in bed 22 and/or in the room in which bed 22 is situated as shown in FIG. 5. In the illustrative example, a network 218 of the healthcare facility includes a wireless ethernet bridge 220 which communicates wirelessly with each of modules 200 if modules 200 are of the type that communicate wirelessly as indicated by phantom lines 222 in FIG. 5. Alternatively, modules 200 may couple to network 218 by wired communications links as indicated by lines 224 in FIG. 5. As further shown in FIG. 5, a plurality of network appliances 226 are coupled to network 218. Appliances 226 may include other beds, other computer devices, other communication modules (like modules 26, 39, 74, 196, 198, 200), room centric services (like those associated with block 214), and any other equipment configured to couple to network 218.

Figure 6:
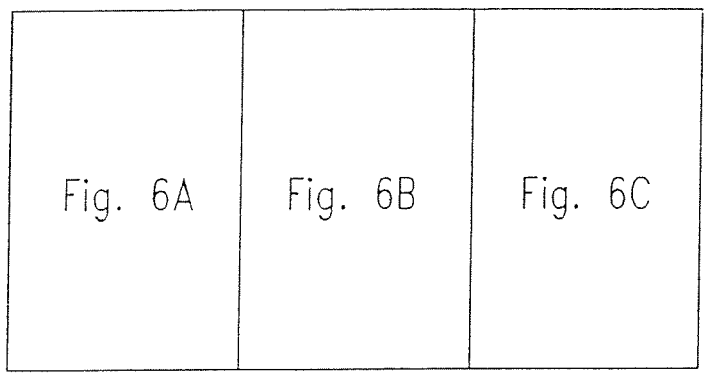
FIG. 6 is a block diagram map showing how to lay out FIGS. 6A-6C to form a block diagram of the circuitry of the bed.
Figure 6A:
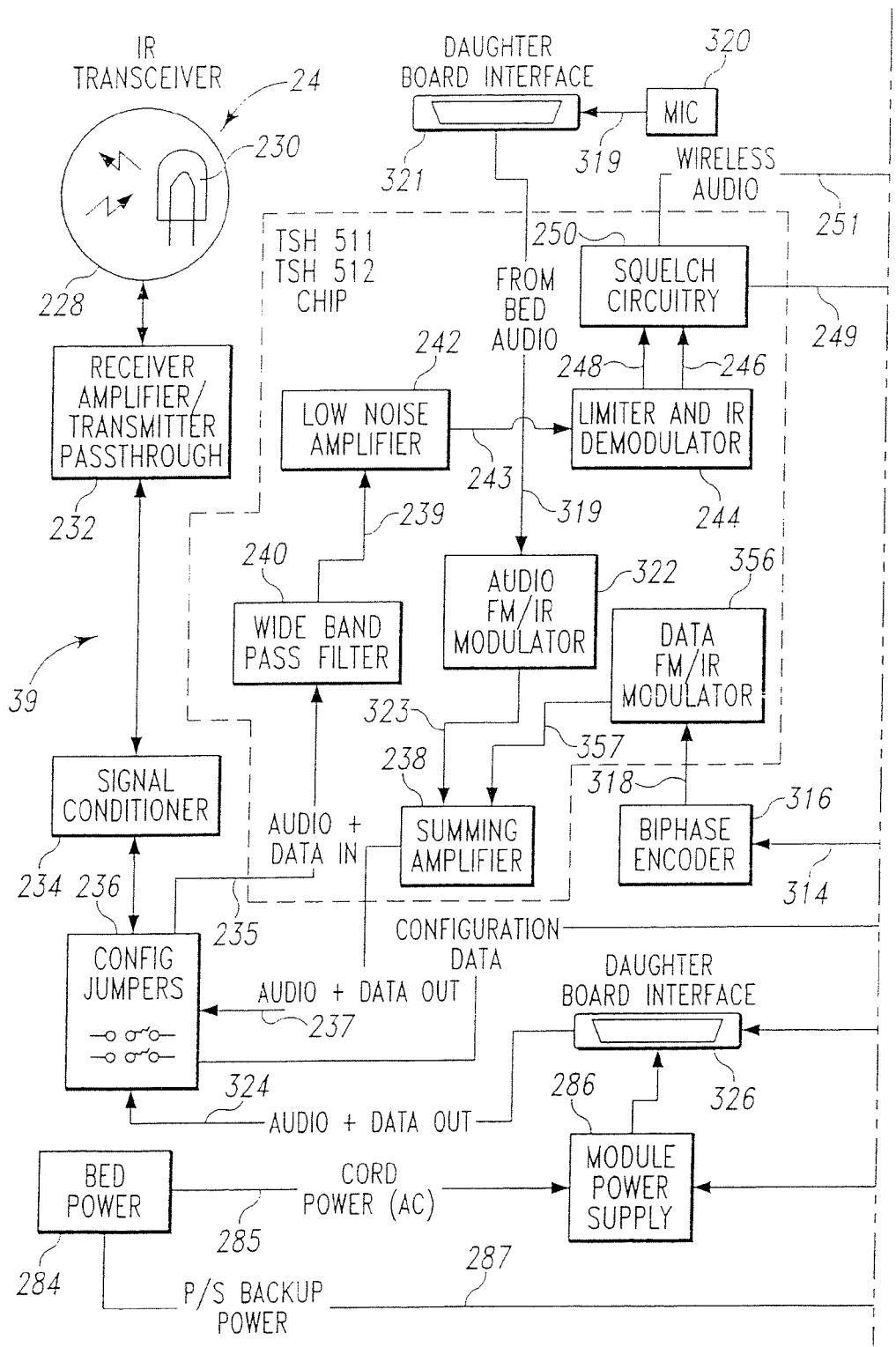
Figure 6B:
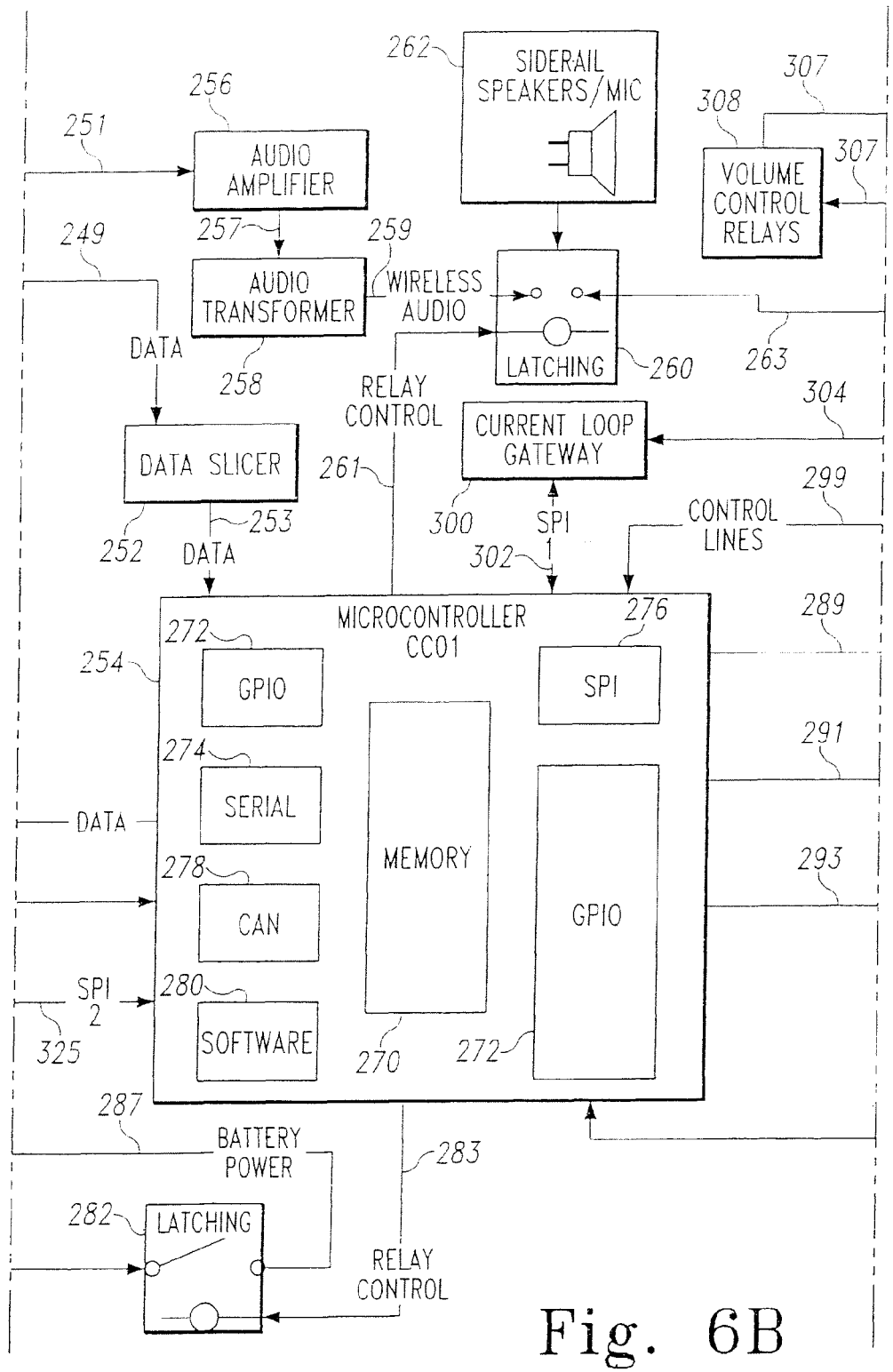
Figure 6C:
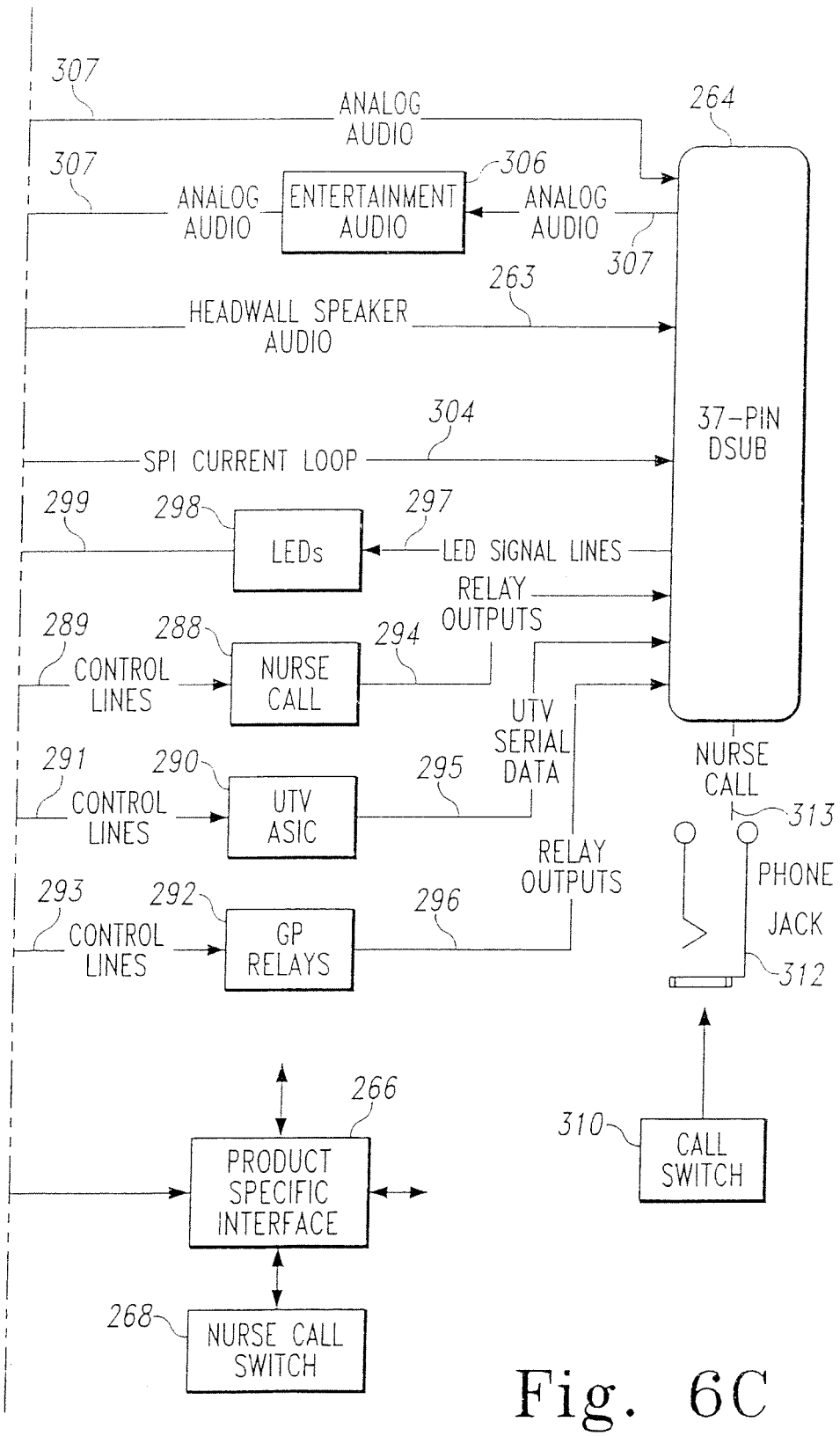

Referring now to FIGS. 6A-6C, which is a block diagram showing more detail about the circuitry of one embodiment of device 22 and cable assembly 39, circuitry 24 includes an IR transceiver 228. Transceiver 228 comprises photodiodes 230, at least one of which is a photoemitter and at least one of which is a photodetector. The photodiodes 230 of transceiver 228 are coupled to a circuit board of circuitry 24 situated in plug body 30. The at least one photodiode 230 which operates as the photoemitter of transceiver 228 emits a first FMIR signal and the at least one photodiode 230 which operates as the photodetector of transceiver 228 receives a second FMIR signal. Transceiver 228 is coupled to a receiver amplifier/transmitter passthrough circuit 232, shown in FIG. 6A, which is included as part of circuitry 24 in plug body 230 in some embodiments. Circuit 232 is coupled to a signal conditioner 234. The signals being transmitted and received by transceiver 228 pass through conditioner 234 and circuit 232 for amplification and/or conditioning in any desired manner.

A configuration jumper 236 is coupled to conditioner 234 as shown in FIG. 6A. Jumper 236 receives a mixed audio-and-data out signal 237 from a summing amplifier 238, which audio-and-data out signal 237 is transmitted from transceiver 228 after being conditioned by conditioner 234 and after passing through circuit 232. In addition, a mixed audio-and-data in signal 235 is communicated to a wide band pass filter 240 from jumper 236, which audio-and-data in signal 235 was received by transceiver 228, amplified by circuit 232, and conditioned by conditioner 234 prior to receipt by jumper 236. Thus, the FMIR signals transmitted and received by the photodiodes 330 of transmitter 228 are mixed signals that contain both audio and data portions.

A filtered audio-and-data in signal 239 is output from filter 240 and is input into a low noise amplifier 242. An amplified and filtered audio-and-data in signal 243 is output from amplifier 242 and is input into a limiter and IR demodulator circuit 244. Circuit 244 demodulates signal 243 received from amplifier 242 at two different frequencies, one of which corresponds to the carrier frequency associated with the audio portion of mixed audio-and-data 235 in signal and the other of which corresponds to the carrier frequency associated with the data portion of mixed audio-and-data in signal 235. Thus, circuit 244 outputs a data signal 246 and an audio signal 248, which signals 246, 248 are input into squelch circuitry 250.

A squelched data signal 249 and a squelched audio signal 251 are output from circuitry 250 as shown in FIG. 6A. Squelched data signal 249 is a coded pulse signal that is input into a data slicer 252, shown in FIG. 6B. Data slicer 252 decodes signal 249 and outputs a digital data signal 253 which comprises Universal Asynchronous Receiver Transmitter (UART) packets of data communicated to a microcontroller 254 of device 22. Squelched audio signal 251 is input into an audio amplifier 256 and an amplified audio signal 257 is output from amplifier 256 as shown in FIG. 6B. Signal 257 is input into an audio transformer 258 which outputs an audio signal 259 that is input into a latching device 260. Latching device 260 is controlled by a relay control signal 261 output from microcontroller 254. Signal 261 controls whether latching device 260, which comprises one or more relays in some embodiments, is in a first position in which audio signal 259 is coupled to a speaker 262 of device 22 or a second position in which a headwall speaker audio signal 263 received by a 37-pin connector or port 264, shown in FIG. 6C, is coupled to speaker 262. If microcontroller 254 is signaled that sensor 98 of module 26 senses the presence of magnet 110 of plug 20, then microcontroller 254 configures signal 261 to move latching device 260 to the first position.

The audio portion of the FMIR signal which is received by transceiver 228 and which is sounded through speaker 262 after being processed in the manner discussed above includes, for example, voice data (human or prerecorded) originating at a master nurse call station, voice data originating at another station similar to station 82 but located in another patient room, television sound, radio sound, and/or an audible alarm signal. The data portion of the FMIR signal which is received by transceiver 228 and which is communicated to microcontroller 254 after being processed in the manner discussed above may be any of a number of different data signals, such as alarm signals, signals for controlling functions of device 22, interrogation signals to request that microcontroller 254 respond with certain data, and signals for controlling additional devices that are coupled to microcontroller 254 via at least one product specific interface 266, shown in FIG. 6C. Examples of devices that may couple to the at least one product specific interface 266 include, for example, patient monitoring devices (e.g., EKG's, EEG's, blood pressure monitors, pulse oximetry equipment, respiration monitors), patient care equipment (e.g., intravenous fluid infusion devices, drug infusion devices, ventilators), and bed control devices, such as hand held pendants. In the illustrative example, a nurse call switch 268 is coupled to interface 266.

As shown diagrammatically in FIG. 6B, microcontroller 254 includes memory 270, a pair of general purpose input/output interfaces 272, a serial interface 274, a serial peripheral interface (SPI) 276, a controlled architecture network (CAN) interface 278, and software 280 which is executed by a central processing unit (CPU) (not shown) of the microcontroller 254. The various interfaces 272, 274, 276, 278 couple to devices and circuitry included in bed 22 as is known by those skilled in the art. An example of a known bed having a CAN system is the VersaCare™ bed available from Hill-Rom Company, Inc.

Microcontroller 254 controls a latching device 282, shown in FIG. 6B, via a relay control signal 283. Signal 283 controls whether latching device 282 is in a first position or in a second position. If device 282 is in the first position, a bed power circuit 284, shown in FIG. 6A, delivers cord power (AC) 285 from cable assembly 39 to a module power supply circuit 286 which, in turn, delivers power after any needed power conversion or regulation to the various components of bed 22 that require power to operate. If device 282 is in the second position, circuit 284 delivers backup battery power to circuit 286 which, in turn, delivers power to at least some of the various components of bed 22 that require power to operate.

Microcontroller 254 is coupled to a nurse call circuit 288, a universal television application specific integrated circuit (UTV ASIC) 290, and a set of general purpose relays 292, shown in FIG. 6C, by first control lines 289, second control lines 291, and third control lines 293, respectively. The signals that microcontroller 254 sends to circuit 288, UTV ASIC 290, and relays 292 to control these portions of device 22 are determined by signals received via one or more of interfaces 272, 274, 276, 278 from user input devices, such as buttons on a control panel of device 22 or on a hand-held control unit of device 22, that are manipulated by a user, such as a patient or caregiver of bed 22. Circuit 288, UTV ASIC 290, and Relays 292 provide relay outputs 294, UTV serial data 295, and relay outputs 296, respectively, to connector 264 as shown in FIG. 6C. In some embodiments, nurse call circuit 288 comprises a relay that closes in response to a patient placing a nurse call with switch 268.

UTV ASIC 290 comprises circuitry that controls the operation of a television in the patient room and, in some embodiments, UTV ASIC 290 is configured to output the appropriate data signals to control multiple brands of televisions. In some embodiments, general purpose relays 292 are coupled to motors, such as motors of linear actuators, that are operated to move various portions of bed 22. Such movements of bed 22 may include raising or lowering a head section of bed 22, raising or lowering a thigh or foot section of bed 22, raising or lowering an upper frame of bed 22 relative to a base frame of bed 22, and tilting the upper frame of bed 22 relative to the base frame of bed 22.

A set of LED's 298 are coupled to connector 264 by LED signal lines 297 and to microcontroller 254 by control lines 299. Each of the LED's correspond to various ones of the functions of bed 22 that are controlled by or monitored by microcontroller 254 and are turned on or off (or are operated to shine one color or another color) to indicate a status of the associated function. A current loop gateway circuit 300 sends and/or receives SPIT signals 302 to and/or from microcontroller 254. Circuit 300 also sends and/or receives SPI current loop signals 304 to and/or from connector 264 as shown in FIGS. 6B and 6C. In addition, an entertainment audio circuit 306 and a set of volume control relays 308 are coupled to each other and to connector 264 by analog audio lines 307. In some embodiments, circuit 306 and relays 308 are coupled to microcontroller 254 to be controlled and/or monitored by microcontroller 254. Optionally, a separate nurse call switch 310 may be coupled to a phone jack 312 which, in turn, is coupled to connector 264 by a nurse call line 313. In some embodiments, microcontroller 254 monitors the status of switch 310 to determine whether switch 310 has been used to place a nurse call.

Connector 264 is provided on bed 22 so that, in the event that a wired connection from bed 22 to the network of the healthcare facility is desired, such a wired connection may be accomplished, for example, by coupling connector 264 to interface unit 80, shown in FIG. 1, with an appropriately configured cable assembly having 37-pin connectors at each end. However, according to this disclosure, such a wired connection is not necessary because any data and audio that would otherwise be sent to or received from the network by bed 22 via connector 264, is communicated wirelessly to and/or from transceiver 228. Thus, any data to be sent from bed 22 is output from microcontroller 254 as a digital data signal 314, such as a serial data signal.

Data signal 314 comprises UART packets of data from microcontroller 254 that are input into a biphase encoder 316, shown in FIG. 6A, which converts the digital data of signal 314 into a coded pulse signal 318. For example, in one embodiment, a logic level "0" bit from microcontroller 254 is coded as a single 200 microsecond pulse and a logic level "1" bit from microcontroller 254 is coded as two 100 microseconds pulses. A first amount of spacing is provided between the two 100 microsecond pulses and a transition code is transmitted between the bits of data. Signal 318 is input into a Data FM/IR Modulator 356 which modulates signal 318 at a predetermined carrier frequency to produce a modulated data signal 357 which is input into summing amplifier 238.

Any audio signals from bed 22, such as, for example, an audio signal 319 originating from a microphone 320 which is provided on bed 22 and which is coupled to a daughter board interface 321, is input in an FM/IR modulator 322. In alternative embodiments, speaker 262 may also serve as a microphone and may output an audio signal that is input into modulator 322. A modulated audio signal 323 is output from modulator and is input into summing amplifier 238, which mixes signals 318, 323 to produce the mixed audio-and-data out signal 237 which is transmitted from transceiver 228 after being conditioned by conditioner 234 and passed through circuit 232.

In alternative embodiments, a second audio-and-data out signal 324 may originate on a circuit board (not shown) that is coupled to a daughter board interface 326. Such a circuit board may receive and/or transmit an SPI2 signal 325 to and/or from microcontroller 254 as shown in FIGS. 6A and 6B. Such a circuit board may also receive power from circuit 286. Signal 324 is coupled to jumper 236 and is transmitted by transceiver 228 along with signal 237 or in lieu of signal 237 after signal 324 is conditioned by conditioner 234 and passed through circuit 232.

Figure 7:
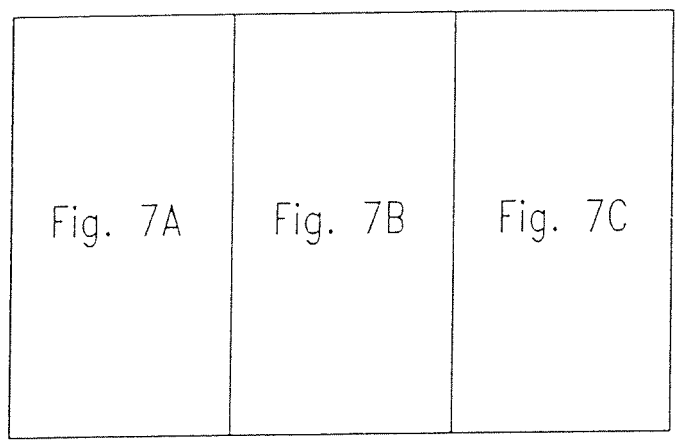
FIG. 7 is a block diagram map showing how to lay out FIGS. 7A-7C to form a block diagram of the circuitry of the outlet module and the wall module.
Figure 7A:
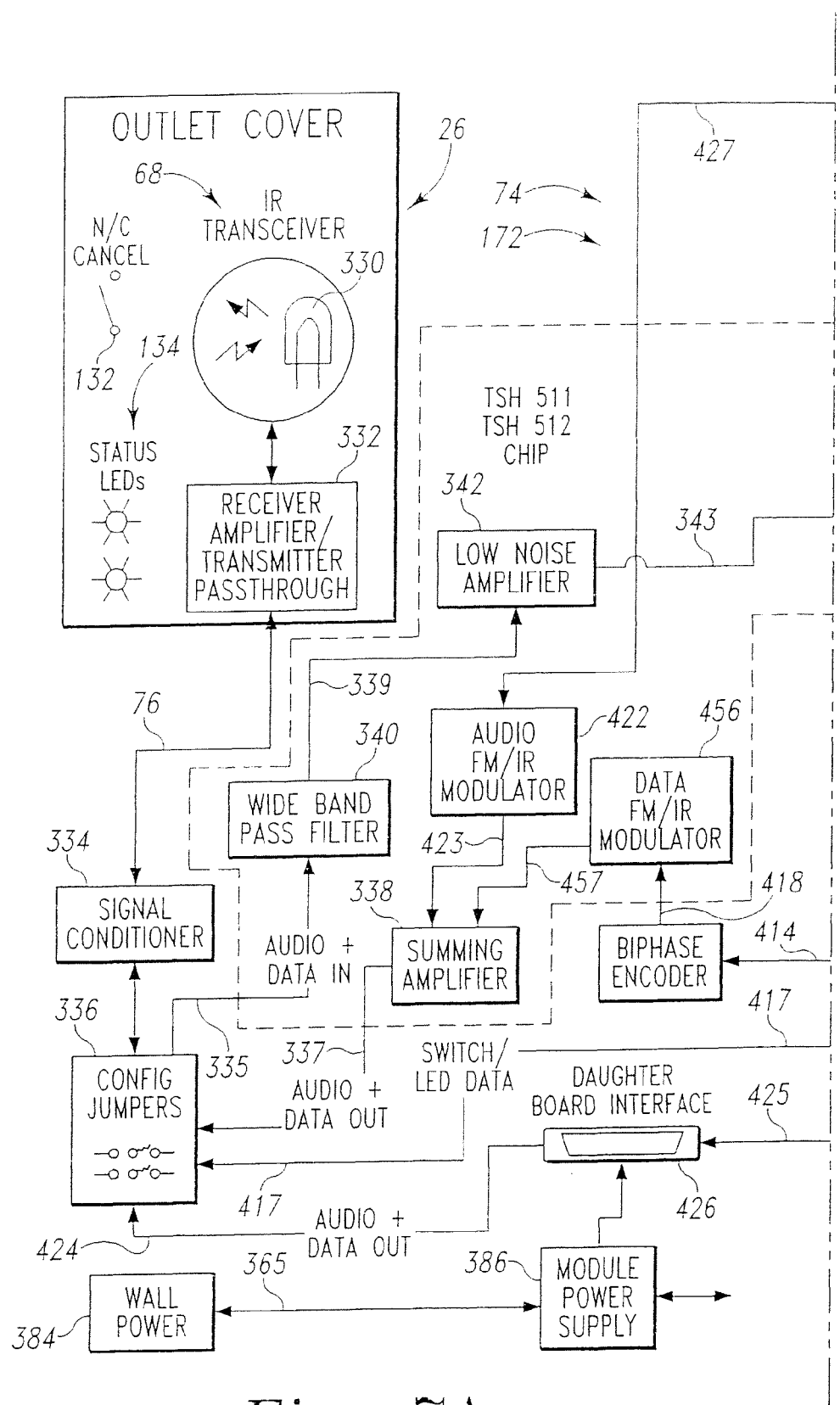
Figure 7B:
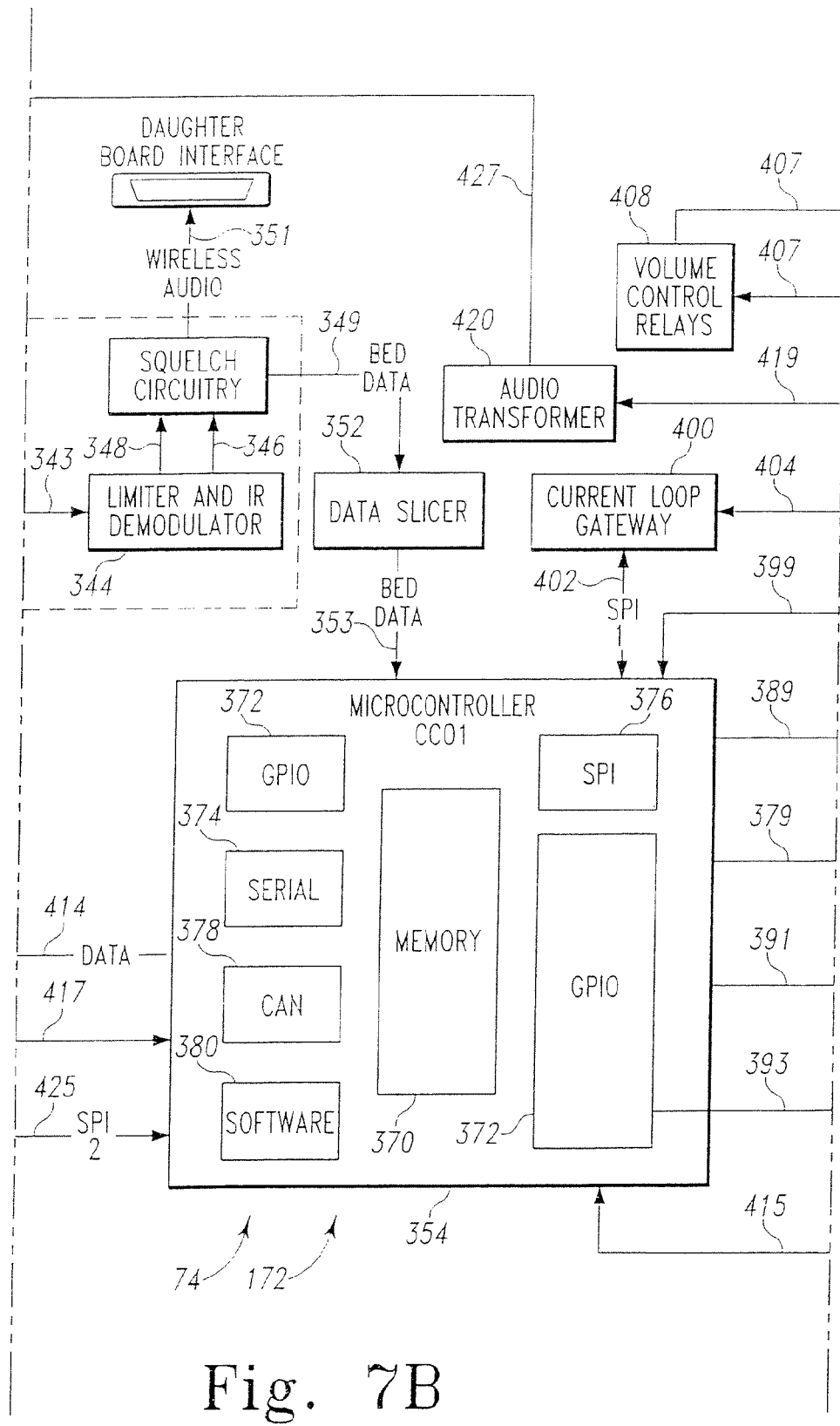
Figure 7C:
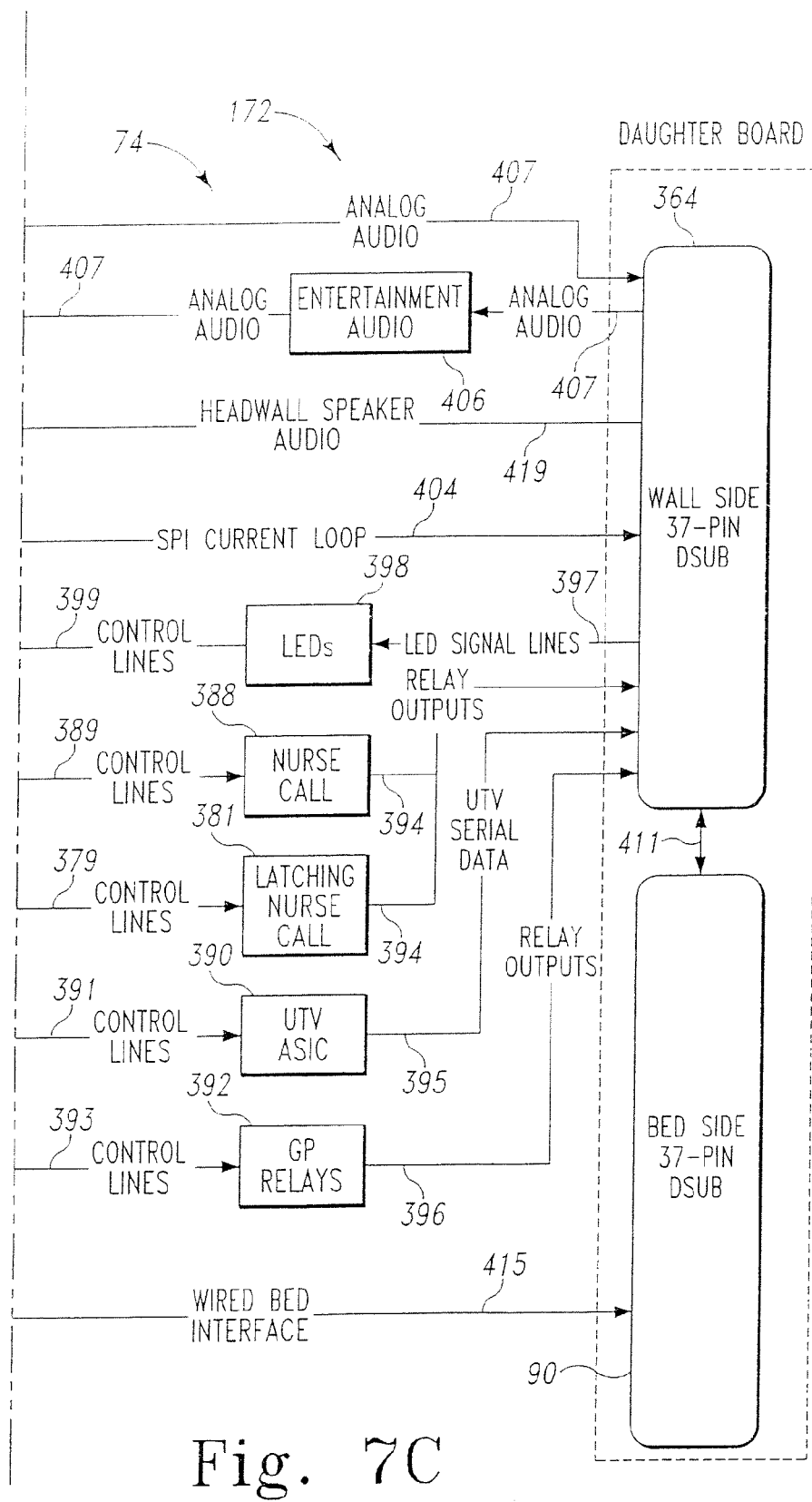

Referring now to FIGS. 7A-7C, which is a block diagram showing more detail about the circuitry 68 of one embodiment of outlet module 26 and the circuitry 172 of one embodiment of wall module 74, circuitry 68 includes an IR transceiver 328. Transceiver 328 communicates wirelessly with transceiver 228 and comprises photodiodes 330, at least one of which is a photoemitter and at least one of which is a photodetector. Referring briefly to FIG. 3, the photodiodes of transceiver 328 are contained in a housing 329 which is mounted to circuit board 130 and which is positioned to aim the photodiodes of circuitry 68 through lens 112 toward the photodiodes of circuitry 24 of plug 20. Thus, the photodiodes 230, 330 of transceivers 228, 328 send and receive wireless signals in a direction that is substantially perpendicular to the direction that prongs 32, 34, 36 extend from plug body 30. Referring once again to FIG. 7A, nurse call cancel button 132 is shown diagrammatically as a switch and LED 134 is shown diagrammatically as two separate LED's.

As will become apparent in the discussion below, the circuitry 172 of module 74 is very nearly the same as the circuitry of bed 22 discussed above in connection with FIGS. 6A-6C. Thus, in the illustrative embodiment, module 74 operates as a bed emulator. As such, the network of the healthcare facility receives signals from and provides signals to module 74 just as if the network were connected directly to the circuitry of bed 22 via connector 264.

The at least one photodiode 330 which operates as the photoemitter of transceiver 328 emits a third FMIR signal and the at least one photodiode 330 which operates as the photodetector of transceiver 328 receives a fourth FMIR signal (the first and second FMIR signals were discussed above in connection with photodiodes 230 of transceiver 228). Transceiver 328 is coupled to a receiver amplifier/transmitter passthrough circuit 332, shown in FIG. 7A, which is included as part of circuitry 68 in module 26. Circuit 332 is coupled to a signal conditioner 334 of circuitry 172 by data cable 76. The signals being transmitted and received by transceiver 328 pass through conditioner 334 and circuit 332 for amplification and/or conditioning in any desired manner.

A configuration jumper 336 is coupled to conditioner 334 as shown in FIG. 7A. Jumper 336 receives a mixed audio-and-data out signal 337 from a summing amplifier 338, which audio-and-data out signal 337 is transmitted from transceiver 328 to transceiver 228 after being conditioned by conditioner 334 and after passing through circuit 332. In addition, a mixed audio-and-data in signal 335 is communicated to a wide band pass filter 340 from jumper 336, which audio-and-data in signal 335 was received by transceiver 328 from transceiver 228, amplified by circuit 332, and conditioned by conditioner 334 prior to receipt by jumper 336. Thus, the FMIR signals transmitted and received by the photodiodes of transmitter 328 are mixed signals that contain both audio and data portions.

A filtered audio-and-data in signal 339 is output from filter 340 and is input into a low noise amplifier 342. An amplified and filtered audio-and-data in signal 343 is output from amplifier 342, as shown in FIG. 7A, and is input into a limiter and IR demodulator circuit 344 as shown in FIG. 7B. Circuit 344 demodulates signal 343 received from amplifier 342 at two different frequencies, one of which corresponds to the carrier frequency associated with the audio portion of mixed audio-and-data in signal 335 and the other of which corresponds to the carrier frequency associated with the data portion of mixed audio-and-data in signal 335. Thus, circuit 344 outputs a data signal 346 and an audio signal 348, which signals 346, 348 are input into squelch circuitry 350.

A squelched bed data signal 349 and a squelched audio signal 351 are output from circuitry 350 as shown in FIG. 7B. Squelched bed data signal 349 is a coded pulse signal that is input into a data slicer 352. Data slicer 352 decodes signal 349 and outputs a digital bed data signal 353 which comprises UART packets of data communicated to a microcontroller 354 of circuitry 172 of module 74. Squelched audio signal 351 is coupled to a daughter board interface 355 so that optional circuitry (not shown) coupled to interface 355 receives audio signal 351 for subsequent processing. In alternative embodiments, audio signal 351 is input into an audio amplifier (not shown) which amplifies audio signal 351 and outputs the amplified audio signal to a 37-pin connector 364 shown in FIG. 7C for subsequent connection to the network of the healthcare facility.

The audio portion of the FMIR signal which is received by transceiver 328 and which eventually becomes audio signal 351 after being processed as described above may be, for example, voice data originating at microphone 320, shown in FIG. 6A. The data portion of the FMIR signal which is received by transceiver 328 and which is communicated to microcontroller 354 after being processed in the manner discussed above may be any of a number of different data signals, such as alarm signals, signals relating to the status of functions of device 22, interrogation signals to request that microcontroller 354 respond with certain data, and signals relating to the status of any additional devices that are coupled to microcontroller 254 via interface 266 as discussed above in connection with FIGS. 6B and 6C.

As shown diagrammatically in FIG. 7B, microcontroller 354 includes memory 370, a pair of general purpose input/output interfaces 372, a serial interface 374, a serial peripheral interface (SPI) 376, a controlled architecture network (CAN) interface 378, and software 380 which is executed by a central processing unit (CPU) (not shown) of the microcontroller 354. The various interfaces 372, 374, 376, 378 couple to circuitry provided in module 74 to emulate any devices or circuitry of bed 22 that are coupled to interfaces 272, 274, 276, 278 of microcontroller 254. A wall power circuit 384, shown in FIG. 7A, delivers power via one or more power lines 365 to a module power supply circuit 386 which, in turn, delivers power after any needed power conversion or regulation to the various components of module 74 that require power to operate.

Microcontroller 354 is coupled to a nurse call circuit 388, a latching nurse call circuit 381, a universal television application specific integrated circuit (UTV ASIC) 390, and a set of general purpose relays 392, shown in FIG. 7C, by first control lines 389, second control lines 279, third control lines 391 and fourth control lines 393, respectively. The signals that microcontroller 354 sends to circuits 381, 388, UTV ASIC 290, and relays 390 to control these portions of module 74 are determined by signals received wirelessly by transceiver 330. Circuits 381, 388, UTV ASIC 390, and Relays 390 provide relay outputs 394, UTV serial data 395, and relay outputs 396, respectively, to connector 364 as shown in FIG. 7C. UTV ASIC 390 comprises circuitry that controls the operation of a television in the patient room and, in some embodiments, UTV ASIC 390 is configured to output the appropriate data signals to control multiple brands of televisions. It will be appreciated that the relays 392 are controlled to mimic or emulate the positions (i.e., opened or closed) of general purpose relays 292 which, in some embodiments, are coupled to motors that are operated to move various portions of bed 22, as described above. However, in the illustrative embodiment, relays 392 are not actually coupled to any motors but simply provide signals to connector 364 to indicate to the network the status of the counterpart relays 292.

A set of LED's 398 are coupled to connector 364 by LED signal lines 397 and to microcontroller 354 by control lines 399. Each of the LED's 398 correspond to various ones of the LED's 298 that, in turn, correspond to functions of bed 22. A current loop gateway circuit 400 sends and/or receives SPI1 signals 402 to and/or from microcontroller 354. Circuit 400 also sends and/or receives SPI current loop signals 404 to and/or from connector 364 as shown in FIGS. 7B and 7C. In addition, an entertainment audio circuit 406 and a set of volume control relays 408 are coupled to each other and to connector 364 by analog audio lines 407. In some embodiments, circuit 406 and relays 408 are coupled to microcontroller 354 to be controlled and/or monitored by microcontroller 354.

Connector 90 is wired to connector 364 by lines 411 and is coupled to microcontroller 356 by a wired bed interface line 415. Thus, if a wired connection is provided between bed 22 and connector 90 with an appropriately configured cable assembly having 37-pin connectors at each end, then signals associated with the various pins of connector 90 are provided to corresponding ones of the pins of connector 364 by lines 411 for communication with, monitoring of, and/or control of the various components of circuitry 172 that are coupled to connector 364. Signals on line 415 indicate to microcontroller 354 whether or not bed 22 is wired to connector 90.

Data regarding the status of button 132 and LED 134 are communicated from jumper 336 to microcontroller 354 by switch/LED data lines 417 as shown in FIGS. 7A and 7B. Any data to be sent from microcontroller 354 to bed 22 is output by microcontroller 354 as a digital data signal 414 that is input into a biphase encoder 416, shown in FIG. 7A. Data signal 414 comprises UART packets of data from microcontroller 354 that are converted by biphase encoder 316 into a coded pulse signal 418. In one embodiment, the pulses of signal 418 are coded in the same manner that the pulses of signal 318 are coded as described above. Signal 418 is input into a Data FM/IR Modulator 456 which modulates signal 418 at a predetermined carrier frequency to produce a modulated data signal 457 which is input into summing amplifier 338.

Any audio signals received by connector 364 from the network, such as, for example, a headwall speaker audio signal 419 is input into an audio transformer 420. Transformer 420 outputs a transformed audio signal 427 that is input into an FM/IR modulator 422. A modulated audio signal 423 is output from modulator 422 and is input into summing amplifier 338, which mixes signals 418, 423 to produce the mixed audio-and-data out signal 337 which is transmitted from transceiver 328 after being conditioned by conditioner 334 and passed through circuit 332.

In alternative embodiments, a second audio-and-data out signal 424 may originate on a circuit board (not shown) that is coupled to a daughter board interface 426. Such a circuit board may receive and/or transmit an SPI2 signal 425 to and/or from microcontroller 354 as shown in FIGS. 7A and 7B. Such a circuit board may also receive power from circuit 386. Signal 424 is coupled to jumper 336 and is transmitted by transceiver 328 along with signal 337, or in lieu of signal 337, after signal 424 is conditioned by conditioner 334 and passed through circuit 332.

As is apparent from the above discussion, the bidirectional wireless communication between plug 20 and module 26 is established by a first mixed FMIR signal that is transmitted from transceiver 228 of plug 20 to transceiver 328 of module 26 across gap 72 and by a second mixed FMIR signal that is transmitted from transceiver 328 of module 26 to transceiver 228 of plug 20 across gap 72. The first mixed FMIR signal includes an audio portion modulated at a first carrier frequency and a data portion modulated at a second carrier frequency. The second mixed FMIR signal includes an audio portion modulated at a third carrier frequency and a data portion modulated at a fourth carrier frequency. While the four different carrier frequencies may be any desired frequencies, in one embodiment, the first carrier frequency is 2.3 Megahertz (MHz), the second carrier frequency is 4.0 MHz, the third carrier frequency is 2.8 MHz, and the fourth carrier frequency is 5.0 MHz.

The audio portions of the FMIR signals transmitted between transceivers 228, 328 remain analog throughout the transmission and processing. These audio signals are frequency modulated similar to the manner in which FM radio signals are frequency modulated. However, instead of being transmitted by an RF antenna, the audio signals are transmitted by photodiodes 230, 330 which, in some embodiments, are high speed IR LED's. The demodulators 244, 344 are tuned to the appropriate carrier frequencies of the audio portions of the FMIR signals. The data portions of the FMIR signals are frequency modulated in basically the same manner as the audio signals, but the data being modulated is a coded pulse signal that, in one embodiment, has a bandwidth of about 10 kilohertz (kHz).

In the illustrative embodiment, a model no. TSH511 and a model no. TSH512 chipset available from STMicroelectronics of Geneva, Switzerland is used in the circuitry of device 22 and in the circuitry 172 of module 74. As indicated by the dotted line box in FIG. 6A, the TSH511/TSH512 chipset of bed 22 comprises summing amplifier 238, wide band pass filter 240, low noise amplifier 242, limiter and IR demodulator 244, squelch circuitry 250, audio FM/IR modulator 322, and data FM/IR modulator 356. Similarly, as indicated by the dotted line box in FIGS. 7A and 7B, the TSH511/TSH512 chipset of module 74 includes summing amplifier 338, wide band pass filter 340, low noise amplifier 342, limiter and IR demodulator 344, squelch circuitry 350, audio FM/IR modulator 422, and data FM/IR modulator 456.

Electric circuit schematics of one implementation of the above-described system in accordance with this disclosure are provided in U.S. Provisional Patent Application Ser. No. (unknown) (attorney docket number 7175-74676) which was filed Aug. 13, 2004 by Express Mail Label No. EL 735253640 US and which is incorporated by reference herein.

Figure 9:
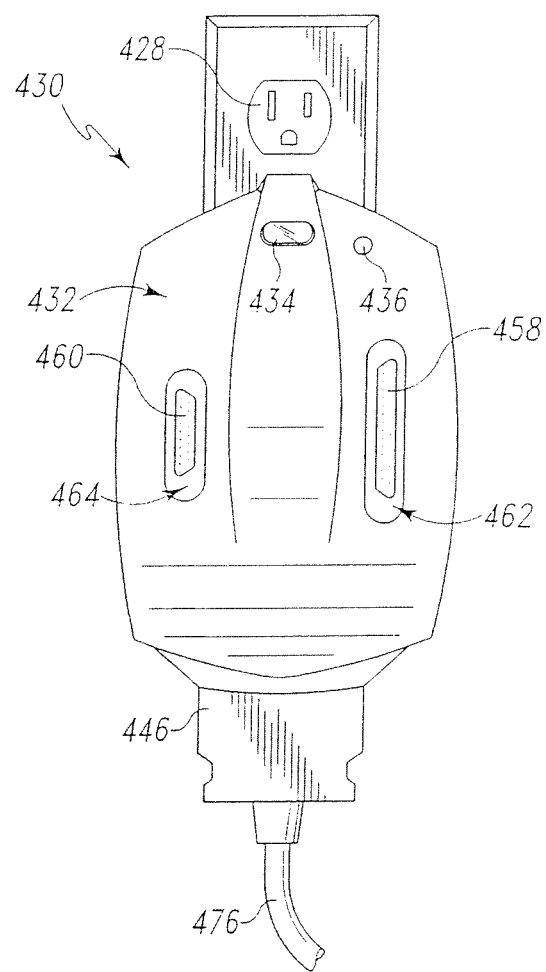
FIG. 9 is a front elevation view of the outlet module and the duplex wall outlet of FIG. 8.
Figure 10:
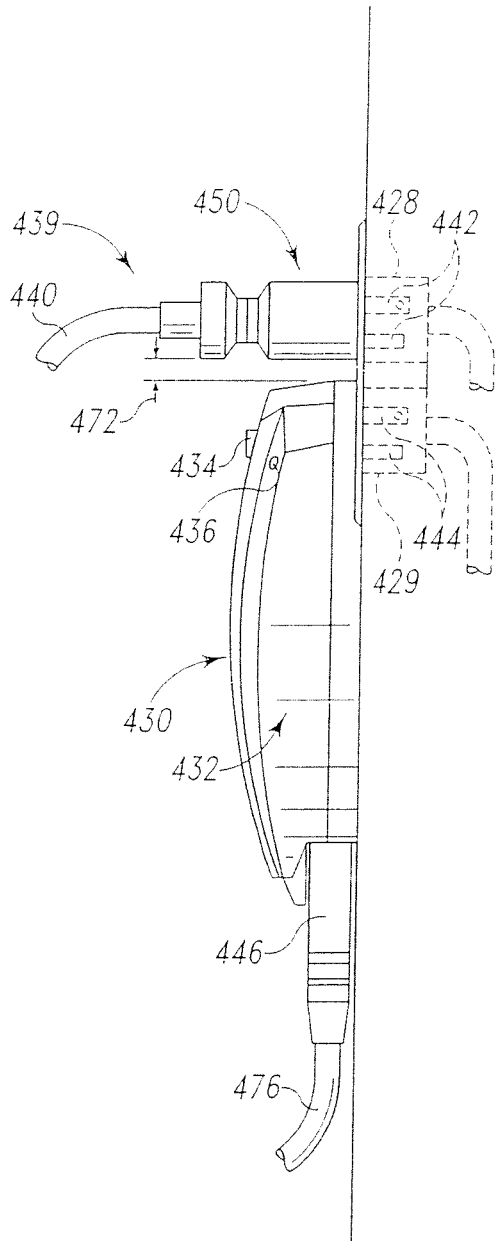
FIG. 10 is a side elevation view of the duplex wall outlet, the power-and-data plug, and the outlet module of FIG. 8.

Referring now to FIGS. 8-10, an alternative embodiment of a combined power-and-data cord assembly 439 has a power-and-data cord 440 terminating at a power-and-data plug 450 that is plugged into a first outlet 428 of a wall duplex outlet. An alternative embodiment of a communication module 430 is plugged into a second outlet 429 of the wall duplex outlet and is configured to communicate wirelessly with circuitry carried by plug 450. The circuitry carried by plug 450 is substantially similar to circuitry 24 of plug 20 described above. Communication module 430 is sometimes referred to herein as the "outlet module." A data cable 476 extends from outlet module 430 to a patient station 482 of a nurse call system of a network of the healthcare facility.

Module 430 has a housing 432 that carries circuitry corresponding to circuitry 68 of module 26, described above, and corresponding to circuitry 172 of module 74, described above. Thus, module 430 is basically a combination of modules 26, 74 into a single communication module. Module 430 has a nurse call cancel button 434, shown in FIGS. 9 and 10, which operates similarly to button 132 of module 26. In addition, module 430 has an LED 436 which operates similarly to LED 134 of module 26.

Because plug 450 couples to outlet 428 above module 430, the circuitry carried by plug 450 is situated in a lower portion of a plug body 452. The circuitry of plug 450 includes a wireless transceiver that communicates wirelessly with a wireless transceiver of module 430 across a gap 472 defined between plug body 452 and module 430 as shown in FIG. 10. Module 430 has a window or lens 454, shown in FIG. 8, that is located at a top portion of housing 432 and that is transmissive to the wireless signals communicated between module 430 and plug 450.

Plug 450 has three electrical contact members 442, two of which are shown in FIG. 10 (in phantom), that receive power and ground from electrical contacts of outlet 428. Module 430 has three members 444, two of which are shown in FIG. 10 (in phantom) that plug into outlet 429. In some embodiments, members 444 are conductive and receive power and ground from electrical contacts of outlet 429. In other embodiments, members 444 are nonconductive and simply provide a means by which module 430 is mounted to outlet 429 beneath plug 450.

Data cable 476 has a first connector 446 at one end and a second connector 448 at an opposite end. Connector 446 couples to a mating connector accessible through a port located at the bottom of module 430 as shown in FIGS. 8-10. Connector 448 couples to a mating connector accessible through a port located on the front of station 482 as shown in FIG. 8. Thus, wireless signals received by the transceiver of module 430 from the wireless transceiver carried by plug 450 are processed by signal-processing circuitry in module 430 and are communicated to station 482 via cable 476. Furthermore, signals received by module 430 from station 482 via cable 476 are processed by the signal-processing circuitry in module 430 and are transmitted wirelessly from the transceiver of module 430 to the transceiver carried by plug 450. In the illustrative example, connector 448 is a 22-pin Phillips™ style connector.

Module 430 has a first auxiliary connector 458 which is accessible through a first port 462 on the front of housing 432 and a second auxiliary connector 460 which is accessible through a second port 464 on the front of housing 432 as shown in FIG. 9. Connector 458 is configured to mate with an appropriately configured connector at the end of a cord extending from any bed, or other device, that does not have a plug 450 and associated circuitry which permits wireless communication with module 430. Thus, when such a cord is connected to connector 458 a wired communications link is established between module 430 and the associated device. Connector 460 is configured to mate with an appropriately configured connector at the end of a cord extending from a hand-held pendant that is used by a patient to control room functions (e.g., temperature and lighting, such as light 466), entertainment functions (e.g., TV and radio), nurse call functions, and/or bed functions. Such a cord extending from a hand-held pendant may be coupled to connector 460 to establish a wired communication link with module 430 simultaneously with, or in lieu of, the wireless communications link between module 430 and plug 450.

Figures 11, 12:
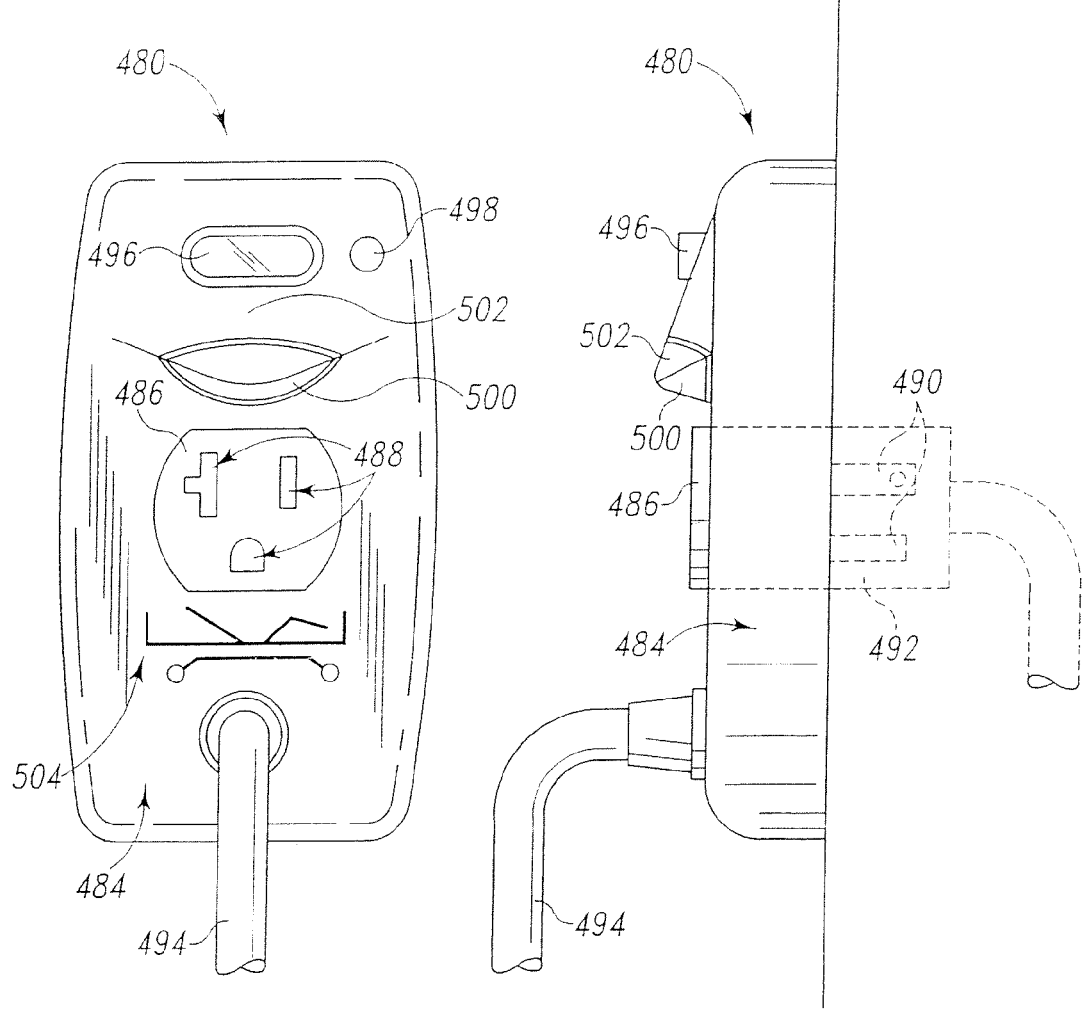
FIG. 11 is a front elevation view of another alternative embodiment of an outlet module showing the outlet module including a power outlet into which a power-and-data plug may be plugged to receive power and to communicate wirelessly with circuitry of the outlet module.
FIG. 12 is a side elevation view of the outlet module of FIG. 11 showing the outlet module having power prongs (in phantom) that plug into a wall outlet (in phantom) to provide power to the power outlet included in the outlet module.

Referring now to FIGS. 11 and 12, an alternative embodiment of a communication module 480 includes a housing 484 and a power outlet 486 into which a power-and-data plug, such as plug 20 of cable assembly 39, may be plugged to receive power and to communicate wirelessly with circuitry of the outlet module 480. Module 480 has circuitry that is configured to communicate wirelessly with circuitry 24 carried by plug 20. Communication module 480 is sometimes referred to herein as the "outlet module." A data cable 494 extends from outlet module 480 and couples either to a network of the healthcare facility or to a wall module like module 74 described above.

Outlet 486 is accessible on the front of housing 484 and has sockets 488 into which prongs 32, 34, 36 of plug 20 may be inserted. Module 480 has three electrical contact members 490, two of which are shown in FIG. 12 (in phantom), that are plugged into a wall outlet 429 to receive power and ground from outlet 492. Power and ground received from outlet 492 by contact members 490 is coupled to electrical contacts in receptacles 488 by suitable electrical conductors. In some embodiments, power and ground received from outlet 492 by contact members 490 is coupled to the circuitry of module 480 after any appropriate processing such as conversion from AC power to suitable DC voltage levels. Thus, module 480 is an adapter which provides power to, and wireless communication with, devices having a cable assembly with a plug like plug 20 that has wireless communication capability and that is coupled to outlet 486 of module 480.

In some embodiments, housing 484 carries circuitry corresponding to circuitry 68 of module 26, described above, and corresponding to circuitry 172 of module 74, described above. In other embodiments, housing 484 carries circuitry corresponding to circuitry 68 but does not have circuitry corresponding to circuitry 172. This disclosure contemplates that module 480 may have any type of circuitry capable to communicating wirelessly with wireless communications circuitry of an associated plug. Module 480 has a nurse call cancel button 496 which operates similarly to button 132 of module 26. In addition, module 480 has an LED 498 which operates similarly to LED 134 of module 26.

In the illustrative example, housing 484 is sized and configured to fit over a standard electrical outlet cover plate (not shown). Module 480 has a window or lens 500 at the bottom of an overhanging portion 502 of housing 484. Portion 502 protrudes away from the main portion of housing 484 by a sufficient amount to allow a wireless transceiver of module 480 to be aimed toward a wireless transceiver of the associated plug that couples to outlet 486. Lens 500 is transmissive to the wireless signals communicated between the transceiver of module 480 and the transceiver of the plug coupled to outlet 486 of module 480. In the illustrative embodiment, module 480 has a bed indicia 504 on the front of housing 484 beneath outlet 486.

Figure 13:
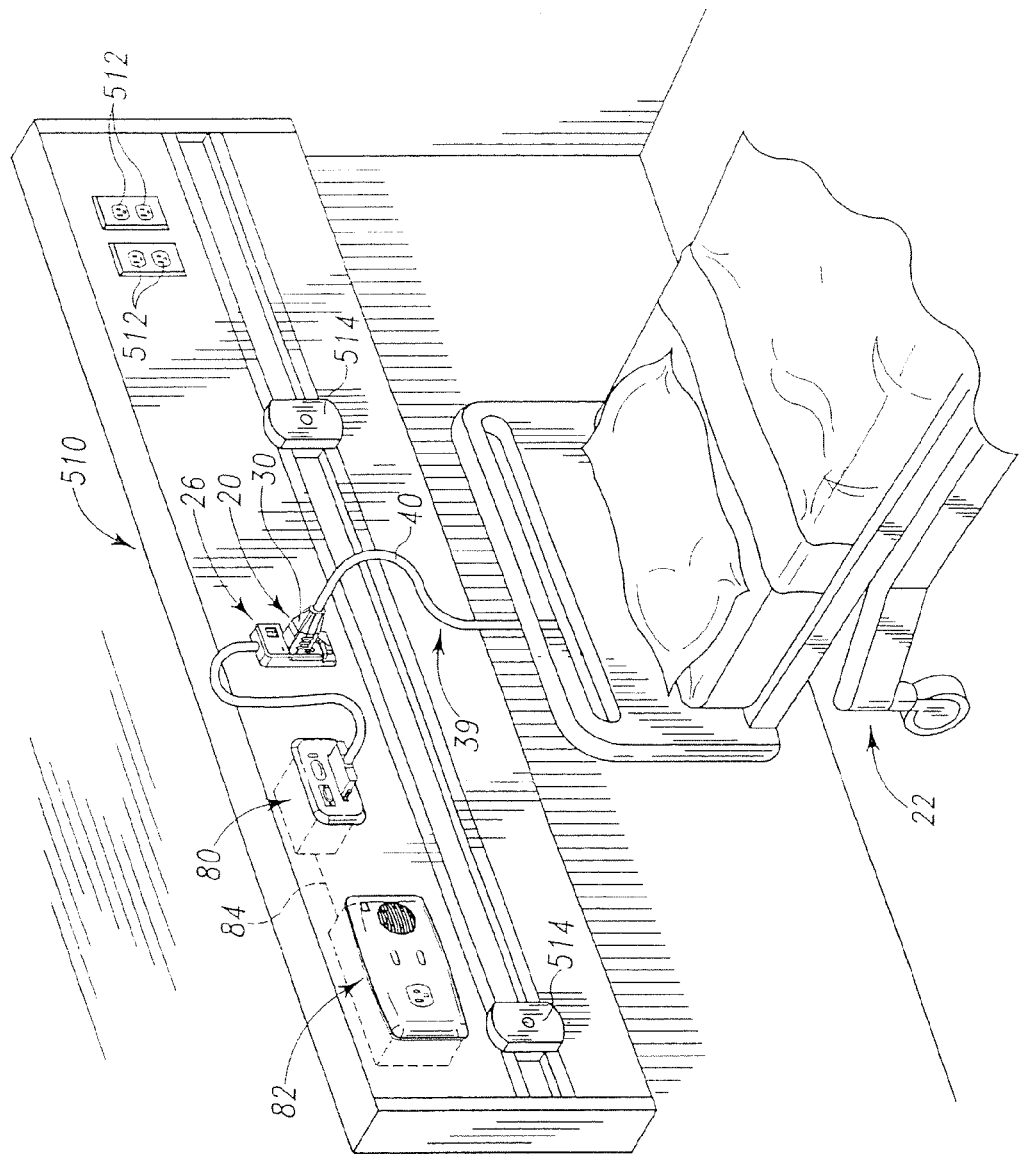
FIG. 13 is a perspective view of yet another embodiment in which a power-and-data plug couples to a wall outlet mounted to a headwall unit in a hospital room, an outlet module adjacent the wall outlet communicating wirelessly with circuitry carried by the plug, the outlet module coupled to an interface unit of a nurse call system by a data cable, and the interface unit being coupled to the headwall unit adjacent a patient station to the nurse call system.

In the above examples, outlet modules 26, 430, 480 are mounted adjacent power outlets that are coupled to walls of associated hospital rooms. It will be appreciated that power outlets are sometimes provided on other types of equipment in hospital rooms and therefore, module 26, 430, 480 may be mounted to any such equipment having power outlets. For example, in an alternative arrangement shown in FIG. 13, outlet module 26 is mounted adjacent a power outlet provided on a piece of architectural equipment 510. While the illustrative architectural equipment 510 comprises a headwall unit having multiple power outlets 512 and gas outlets 514, it is within the scope of this disclosure for modules 26, 430, 480 to be coupled to other types of architectural equipment such as, for example, bed locators, service columns, service chases, flat wall systems, carts, arms, and so forth. Wall module 74 may be coupled to these various types of architectural equipment as well. However, in the example shown in FIG. 13, module 74 is omitted and module 26 communicates with the network via a data cable 516. Data cable 516 terminates at a connector 518 which couples to a data port of interface 80. Wired link 84 between interface 80 and patient station 82 situated in interior spaces of headwall unit 510.

Because some embodiments described herein have a short-range wireless link between device 22 and an associated outlet module, such as one of modules 26, 430, 480, there is little probability, if any, that wireless signals to and/or from one device 22 will get communicated to an outlet module designated for another device in such embodiments having short-range wireless links. In these embodiments, therefore, an association between a particular bed and a particular location in a healthcare facility may be made without any manual entry of data by caregivers.

To associate a particular bed to a particular outlet module and/or to a particular wall module (i.e., communication module), which corresponds to a particular location in a healthcare facility, a unique identifier or address is assigned to each communication module and a unique identifier, such a serial number, is assigned to each device 22. The unique identifiers of the communication modules are stored in memory of the circuitry of each associated communication module and the unique identifiers for devices 22 are stored in the memory of devices 22.

In response to a wireless communications link being established between a particular device 22 and a particular module 26, 430, 480, the unique identifiers are exchanged between devices 22 and one or more of modules 26, 74, 430, 480 and, in some embodiments, are transmitted to the network For example, when sensor 98 senses the proximity of magnet 110, one of the associated module 26, 74, 430, 480 sends a query or interrogation signal to the associated device 22 and the associated device responds with its unique identifier which is stored in memory of the module 26, 74, 430, 480. As a result of being queried, each device 22 sends an interrogation signal to one or more of the associated module 26, 74, 430, 480 and the associated module 26, 74, 430, 480 responds with its unique identifier. Alternatively, the unique identifier of each module 26, 74, 430, 480 may be transmitted along with its initial interrogation signal for storage in the memory of the associated device 22.

In some embodiments, the unique identifiers of devices 22 and modules 26, 74, 430, 480 are communicated only once in response to the initial wireless coupling of a particular device 22 to an associated module 26, 74, 430, 480. In other embodiments, the unique identifiers of devices 22 and modules 26, 74, 430, 480 are communicated periodically. In still other embodiments, the unique identifiers of devices 22 and modules 26, 74, 430, 480 are communicated as part of every packet sent by devices 22 and modules 26, 74, 430, 480. A computer device of the network, such as a Master Nurse Station computer, may keep track of the association between each of devices 22 and the corresponding module 26, 74, 430, 480. Such a computer device may also associate device 22 and/or the corresponding module 26, 74, 430, 480 to other data, such as the patient, caregiver(s) or doctor(s) assigned to the particular device 22. Once device 22, modules 26, 74, 430, 480, and any other computer devices of the network are programmed appropriately, the various associations described above are monitored automatically without the need for caregivers to enter any data or provide any other commands to any devices of the network.

Although each of illustrative modules 26, 430, 480 couple to or mount over the associated power outlet, it is within the scope of this disclosure for modules 26, 430, 480 to be mounted elsewhere. For example, modules 26, 430, 480 may mount to other portions of the walls to which the associated outlets are mounted, either above, below or beside the outlets, or modules 26, 430, 480 may mount to other portions of the architectural equipment, or any other structures for that matter, that are in the vicinity of the associated power outlets.

Although certain embodiments have been described in detail above, variations and modifications exist within the scope and spirit of this disclosure as described and as defined in the following claims.

The invention claimed is:

1. A system for use with a hospital bed having circuitry and a standard AC power outlet spaced from the hospital bed, the system comprising
a cable assembly couplable to the circuitry of the hospital bed, the cable assembly including power conductors and at least one data conductor, the cable assembly having a plug including a first power coupler coupled to the power conductors and a first data coupler coupled to the at least one data conductor, and
a second data coupler mountable adjacent the standard AC power outlet, the second data coupler being configured to couple to the first data coupler when the first power coupler is coupled to the standard AC power outlet.

2. The system of claims 1, wherein the cable assembly includes a junction member and first, second, and third cables extending from the junction member, the first cable having a first portion of the power conductors contained therein, the second cable having a first portion of the at least one data conductor contained therein, and the third cable having second portions of each of the power conductors and the at least one data conductor contained therein such that the third cable serves as a combined power and data cable.

3. The system of claim 2, wherein the first cable terminates at a first power connector that is configured to mate with a second power connector of the hospital bed and wherein the second cable terminates at a first data connector that is configured to mate with a second data connector of the hospital bed.

4. The system of claim 2, wherein the first, second, and third cables are permanently affixed to the junction member.

5. The system of claim 2, wherein at least one of the first, second, and third cables are detachable from the junction member.

6. The system of claim 1, wherein each of the power conductors and each data conductor of the at least one data conductor is encased in its own insulator.

7. The system of claim 1, wherein the cable assembly includes a sheath that surrounds the at least one data conductor and that serves to shield the at least one data conductor, at least partially, from any electromagnetic field produced by AC voltage levels associated with the power conductors.

8. The system of claim 1, wherein the cable assembly comprises a unitary jacket, the power conductors are grouped together within the unitary jacket in a first grouping, and the at least one data conductor comprises a plurality of data conductors that are grouped together in the unitary jacket in a second grouping, and the first and second groupings are spaced apart.

9. The system of claim 1, wherein the plug comprises a plug body and further comprising a plurality of prongs extending from the plug body, each prong of the plurality of prongs being coupled to a respective one of the power conductors, and the first data coupler being spaced apart from the plurality of prongs.

10. The system of claim 1, wherein the power conductors and the at least one data conductors each comprise a metal wire.

11. The system of claim 1, further comprising a sheath surrounding the at least one data conductor and the sheath comprising aluminum and polyethylene.

12. The system of claim 11, further comprising a pleach surrounding the sheath.

13. The system of claim 12, further comprising a ground conductor embedded in the pleach.

14. The system of claim 13, further comprising a jacket in which the pleach and sheath are embedded.

15. The system of claim 1, wherein the second data coupler is included as part of a module that mounts adjacent a face plate of the standard AC power outlet.

16. The system of claim 1, wherein the second data coupler is communicatively coupled with a nurse call system.

17. The system of claim 16, wherein the second data coupler is included as a part of a module that includes a nurse call cancel button that is pressed to cancel a nurse call.

18. The system of claim 1, wherein the first and second data couplers are in wireless communication.

19. The system of claim 1, wherein the first and second data couplers each comprise at least one of a photoemitter and a photodetector.

20. The system of claim 1, wherein data communicated between the first and second data couplers includes voice data.

* * * * *